United States Patent
McLain et al.

(10) Patent No.: US 10,667,818 B2
(45) Date of Patent: Jun. 2, 2020

(54) LOCKOUT ASSEMBLY FOR LINEAR SURGICAL STAPLER

(71) Applicant: ETHICON LLC, Guaynabo, PR (US)

(72) Inventors: Cameron D. McLain, Cincinnati, OH (US); Michael J. Stokes, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 124 days.

(21) Appl. No.: 15/889,370

(22) Filed: Feb. 6, 2018

(65) Prior Publication Data

US 2019/0239882 A1 Aug. 8, 2019

(51) Int. Cl.
*A61B 17/072* (2006.01)
*A61B 17/115* (2006.01)
(Continued)

(52) U.S. Cl.
CPC ...... *A61B 17/115* (2013.01); *A61B 17/07207* (2013.01); *A61B 17/1114* (2013.01);
(Continued)

(58) Field of Classification Search
CPC ............... A61B 17/068; A61B 17/072; A61B 17/07207; A61B 17/115; A61B 2017/07214; A61B 2017/07257; A61B 2017/0725; A61B 2017/07271; A61B 2017/07285; A61B 2090/0801;
(Continued)

(56) References Cited

U.S. PATENT DOCUMENTS

| | | |
|---|---|---|
| 960,300 A | 6/1910 | Fischer |
| 3,078,465 A | 2/1963 | Bobrov |

(Continued)

FOREIGN PATENT DOCUMENTS

| | | |
|---|---|---|
| EP | 0033548 B1 | 5/1986 |
| EP | 0178940 B1 | 1/1991 |

(Continued)

OTHER PUBLICATIONS

U.S. Appl. No. 15/889,363, filed Feb. 6, 2018.

(Continued)

*Primary Examiner* — Scott A Smith
(74) *Attorney, Agent, or Firm* — Frost Brown Todd LLC

(57) ABSTRACT

An apparatus includes a handle assembly, an end effector, a firing assembly, and a lockout assembly. The handle assembly includes first and second arms and a latching lever. The end effector includes first and second jaws and a staple cartridge. The firing assembly is configured to actuate from a pre-fired proximal position toward a distal position in order to staple and sever tissue captured between the first jaw and the second jaw. The lockout assembly is configured to prevent distal translation of the firing assembly in a locked configuration and allow distal translation of the firing assembly in an unlocked configuration. The latching lever is configured to actuate the lockout assembly from the locked configuration to the unlocked configuration in response to the latching lever pivoting the second jaw from a partially closed configuration to a fully closed configuration while the firing assembly is in the pre-fired proximal position.

16 Claims, 33 Drawing Sheets

(51) Int. Cl.
*A61B 17/11* (2006.01)
*A61B 17/3205* (2006.01)
*A61B 90/00* (2016.01)
*A61B 17/068* (2006.01)
*A61B 17/00* (2006.01)

(52) U.S. Cl.
CPC ........ *A61B 17/3205* (2013.01); *A61B 17/068* (2013.01); *A61B 17/072* (2013.01); *A61B 2017/00477* (2013.01); *A61B 2017/0725* (2013.01); *A61B 2017/07257* (2013.01); *A61B 2017/07271* (2013.01); *A61B 2017/07278* (2013.01); *A61B 2017/07285* (2013.01); *A61B 2090/034* (2016.02); *A61B 2090/0801* (2016.02); *A61B 2090/0811* (2016.02); *A61B 2090/0814* (2016.02)

(58) Field of Classification Search
CPC .... A61B 2090/0814; A61B 2090/0811; A61B 2090/034
USPC .. 227/19, 175.1, 175.2, 175.3, 176.1, 180.1; 606/139, 219
See application file for complete search history.

(56) References Cited

U.S. PATENT DOCUMENTS

| | | | |
|---|---|---|---|
| 3,079,606 A | 3/1963 | Bobrov et al. | |
| 3,315,863 A | 4/1967 | O'Dea | |
| 3,317,105 A | 5/1967 | Astafjev et al. | |
| 3,490,675 A | 1/1970 | Green et al. | |
| 4,111,206 A | 9/1978 | Vishnevsky et al. | |
| 4,241,861 A | 12/1980 | Fleischer | |
| 4,290,542 A | 9/1981 | Fedotov et al. | |
| D272,851 S | 2/1984 | Green et al. | |
| D272,852 S | 2/1984 | Green et al. | |
| 4,429,695 A | 2/1984 | Green | |
| 4,520,817 A | 6/1985 | Green | |
| 4,596,351 A | 6/1986 | Fedotov et al. | |
| 4,605,001 A | 8/1986 | Rothfuss et al. | |
| D285,836 S | 9/1986 | Hunt et al. | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,869,415 A | 9/1989 | Fox | |
| 4,892,244 A | 1/1990 | Fox et al. | |
| 4,955,898 A | 9/1990 | Matsutani et al. | |
| 5,065,929 A | 11/1991 | Schulze et al. | |
| 5,083,695 A | 1/1992 | Foslien et al. | |
| 5,129,570 A | 7/1992 | Schulze et al. | |
| 5,141,144 A | 8/1992 | Foslien et al. | |
| 5,156,614 A | 10/1992 | Green et al. | |
| 5,173,133 A | 12/1992 | Morin et al. | |
| 5,221,036 A | 6/1993 | Takase | |
| 5,417,361 A | 5/1995 | Williamson, IV | |
| 5,445,304 A | 8/1995 | Plyley et al. | |
| 5,452,837 A | 9/1995 | Williamson, IV et al. | |
| 5,465,896 A | 11/1995 | Allen et al. | |
| 5,489,058 A | 2/1996 | Plyley et al. | |
| 5,505,363 A | 4/1996 | Green et al. | |
| 5,535,935 A | 7/1996 | Vidal et al. | |
| 5,542,594 A | 8/1996 | McKean et al. | |
| 5,562,241 A | 10/1996 | Knodel et al. | |
| 5,586,711 A | 12/1996 | Plyley et al. | |
| 5,636,779 A | 6/1997 | Palmer | |
| 5,651,491 A | 7/1997 | Heaton et al. | |
| 5,653,373 A | 8/1997 | Green et al. | |
| 5,655,698 A | 8/1997 | Yoon | |
| 5,657,921 A | 8/1997 | Young et al. | |
| 5,673,842 A | 10/1997 | Bittner et al. | |
| 5,680,983 A | 10/1997 | Plyley et al. | |
| 5,718,359 A | 2/1998 | Palmer et al. | |
| 5,785,232 A | 7/1998 | Vidal et al. | |
| 5,816,471 A | 10/1998 | Plyley et al. | |
| 5,871,135 A | 2/1999 | Williamson, IV et al. | |
| 5,878,938 A * | 3/1999 | Bittner ............ A61B 17/07207 227/175.4 |
| 5,908,427 A | 6/1999 | McKean et al. | |
| 5,988,479 A | 11/1999 | Palmer | |
| 6,045,560 A | 4/2000 | McKean et al. | |
| 6,131,789 A | 10/2000 | Schulze et al. | |
| 6,155,473 A | 12/2000 | Tompkins et al. | |
| 6,206,903 B1 | 3/2001 | Ramans | |
| 7,032,799 B2 | 4/2006 | Viola et al. | |
| 7,055,730 B2 | 6/2006 | Ehrenfels et al. | |
| 7,121,446 B2 | 10/2006 | Arad et al. | |
| 7,140,527 B2 | 11/2006 | Ehrenfels et al. | |
| 7,188,758 B2 | 3/2007 | Viola et al. | |
| 7,207,471 B2 | 4/2007 | Heinrich et al. | |
| 7,210,609 B2 | 5/2007 | Leiboff et al. | |
| 7,238,195 B2 | 7/2007 | Viola | |
| 7,278,563 B1 | 10/2007 | Green | |
| 7,293,685 B2 | 11/2007 | Ehrenfels et al. | |
| 7,326,232 B2 | 2/2008 | Viola et al. | |
| 7,334,717 B2 | 2/2008 | Rethy et al. | |
| 7,407,078 B2 | 8/2008 | Shelton, IV et al. | |
| 7,419,081 B2 | 9/2008 | Ehrenfels et al. | |
| 7,422,139 B2 | 9/2008 | Shelton, IV et al. | |
| 7,431,730 B2 | 10/2008 | Viola | |
| 7,472,815 B2 | 1/2009 | Shelton, IV et al. | |
| 7,472,816 B2 | 1/2009 | Holsten et al. | |
| 7,490,749 B2 | 2/2009 | Schall et al. | |
| 7,543,729 B2 | 6/2009 | Ivanko | |
| 7,568,604 B2 | 8/2009 | Ehrenfels et al. | |
| 7,571,845 B2 | 8/2009 | Viola | |
| 7,631,793 B2 | 12/2009 | Rethy et al. | |
| 7,631,794 B2 | 12/2009 | Rethy et al. | |
| 7,635,074 B2 | 12/2009 | Olson et al. | |
| 7,637,410 B2 | 12/2009 | Marczyk | |
| 7,641,091 B2 | 1/2010 | Olson et al. | |
| 7,665,647 B2 | 2/2010 | Shelton, IV et al. | |
| 7,717,312 B2 | 5/2010 | Beetel | |
| 7,721,933 B2 | 5/2010 | Ehrenfels et al. | |
| 7,722,610 B2 | 5/2010 | Viola et al. | |
| 7,740,160 B2 | 6/2010 | Viola | |
| 7,744,628 B2 | 6/2010 | Viola | |
| 7,766,209 B2 | 8/2010 | Baxter, III et al. | |
| 7,810,691 B2 | 10/2010 | Boyden et al. | |
| 7,815,092 B2 | 10/2010 | Whitman et al. | |
| 7,828,189 B2 | 11/2010 | Holsten et al. | |
| 7,837,081 B2 | 11/2010 | Holsten et al. | |
| 7,866,528 B2 | 1/2011 | Olson et al. | |
| 7,905,381 B2 | 3/2011 | Baxter, III et al. | |
| 7,931,182 B2 | 4/2011 | Boyden et al. | |
| 7,942,300 B2 | 5/2011 | Rethy et al. | |
| 7,954,685 B2 | 6/2011 | Viola | |
| 7,954,686 B2 | 6/2011 | Baxter, III et al. | |
| 7,997,469 B2 | 8/2011 | Olson et al. | |
| 8,006,888 B2 | 8/2011 | Viola | |
| 8,028,884 B2 | 10/2011 | Sniffin et al. | |
| 8,070,035 B2 | 12/2011 | Holsten et al. | |
| 8,074,861 B2 | 12/2011 | Ehrenfels et al. | |
| 8,091,754 B2 | 1/2012 | Ehrenfels et al. | |
| 8,113,407 B2 | 2/2012 | Holsten et al. | |
| 8,127,975 B2 | 3/2012 | Olson et al. | |
| 8,152,041 B2 | 4/2012 | Kostrzewski | |
| 8,157,153 B2 | 4/2012 | Shelton, IV et al. | |
| 8,231,040 B2 | 7/2012 | Zemlok et al. | |
| 8,245,901 B2 | 8/2012 | Stopek | |
| 8,256,655 B2 | 9/2012 | Sniffin et al. | |
| 8,257,634 B2 | 9/2012 | Scirica | |
| 8,267,300 B2 | 9/2012 | Boudreaux | |
| 8,272,552 B2 | 9/2012 | Holsten et al. | |
| 8,292,146 B2 | 10/2012 | Holsten et al. | |
| 8,292,148 B2 | 10/2012 | Viola | |
| 8,308,043 B2 | 11/2012 | Bindra et al. | |
| 8,336,753 B2 | 12/2012 | Olson et al. | |
| 8,348,129 B2 | 1/2013 | Bedi et al. | |
| 8,418,907 B2 | 4/2013 | Johnson et al. | |
| 8,464,922 B2 | 6/2013 | Marczyk | |
| 8,496,154 B2 | 7/2013 | Marczyk et al. | |
| 8,496,156 B2 | 7/2013 | Sniffin et al. | |

(56) References Cited

U.S. PATENT DOCUMENTS

| | | |
|---|---|---|
| 8,496,683 B2 | 7/2013 | Prommersberger et al. |
| 8,505,801 B2 | 8/2013 | Ehrenfels et al. |
| 8,544,712 B2 | 10/2013 | Jankowski |
| 8,579,178 B2 | 11/2013 | Holsten et al. |
| 8,636,193 B2 | 1/2014 | Whitman et al. |
| 8,636,939 B2 | 1/2014 | Czernik et al. |
| 8,679,156 B2 | 3/2014 | Smith et al. |
| 8,708,210 B2 | 4/2014 | Zemlok et al. |
| 8,728,118 B2 | 5/2014 | Hinman et al. |
| 8,789,740 B2 | 7/2014 | Baxter, III et al. |
| 8,905,287 B2 | 12/2014 | Racenet et al. |
| 8,915,930 B2 | 12/2014 | Huitema et al. |
| 9,016,541 B2 | 4/2015 | Viola et al. |
| 9,119,617 B2 | 9/2015 | Souls et al. |
| 9,364,219 B2 | 6/2016 | Olson et al. |
| 9,402,629 B2 | 8/2016 | Ehrenfels et al. |
| 9,439,649 B2 | 9/2016 | Shelton, IV et al. |
| 9,451,959 B2 | 9/2016 | Patankar et al. |
| 9,474,525 B2 | 10/2016 | Smith et al. |
| 9,498,213 B2 | 11/2016 | Marczyk et al. |
| 9,561,030 B2 | 2/2017 | Zhang et al. |
| 9,629,812 B2 | 4/2017 | Widenhouse et al. |
| 9,636,113 B2 | 5/2017 | Wenchell |
| 9,636,128 B2 | 5/2017 | Zemlok et al. |
| 9,681,873 B2 | 6/2017 | Smith et al. |
| 9,693,775 B2 | 7/2017 | Agarwal et al. |
| 9,750,502 B2 | 9/2017 | Scirica et al. |
| 9,867,616 B2 | 1/2018 | Marczyk |
| 2005/0222616 A1* | 10/2005 | Rethy .............. A61B 17/07207 606/215 |
| 2006/0180633 A1 | 8/2006 | Emmons |
| 2007/0119901 A1 | 5/2007 | Ehrenfels et al. |
| 2007/0145096 A1 | 6/2007 | Viola et al. |
| 2009/0255974 A1 | 10/2009 | Viola |
| 2009/0308907 A1 | 12/2009 | Nalagatla et al. |
| 2010/0133317 A1 | 6/2010 | Shelton, IV et al. |
| 2011/0290856 A1 | 12/2011 | Shelton, IV et al. |
| 2012/0046689 A1 | 2/2012 | Criscuolo et al. |
| 2012/0286022 A1 | 11/2012 | Olson et al. |
| 2013/0186935 A1 | 7/2013 | Edoga et al. |
| 2013/0190732 A1 | 7/2013 | Slisz et al. |
| 2014/0103091 A1 | 4/2014 | Whitman et al. |
| 2015/0327855 A1 | 11/2015 | Katre et al. |
| 2016/0157890 A1 | 6/2016 | Drake et al. |
| 2016/0262756 A1 | 9/2016 | Patankar et al. |
| 2016/0310136 A1* | 10/2016 | Gupta .............. A61B 17/07207 |

FOREIGN PATENT DOCUMENTS

| | | |
|---|---|---|
| EP | 0669104 A1 | 8/1995 |
| EP | 0770355 A1 | 5/1997 |
| EP | 1382303 B1 | 6/2006 |
| EP | 1702567 A2 | 9/2006 |
| EP | 1728475 A2 | 12/2006 |
| EP | 1977701 B1 | 12/2011 |
| EP | 2452636 A2 | 5/2012 |
| EP | 2305137 B1 | 12/2012 |
| EP | 2308390 B1 | 12/2012 |
| EP | 1693007 B1 | 10/2013 |
| EP | 1862129 B1 | 4/2014 |
| EP | 2550920 B1 | 1/2015 |
| EP | 2532313 B1 | 4/2016 |
| EP | 2532312 B1 | 12/2016 |
| EP | 3155988 A1 | 4/2017 |
| GB | 927936 A | 6/1963 |
| JP | 2001-502575 A | 2/2001 |
| JP | 2007-000657 A | 1/2007 |
| SU | 599799 A1 | 4/1978 |
| WO | WO 1999/045849 A1 | 9/1999 |
| WO | WO 2002/030297 A2 | 4/2002 |
| WO | WO 2003/030742 A2 | 4/2003 |
| WO | WO 2003/094743 A1 | 11/2003 |
| WO | WO 2003/094745 A1 | 11/2003 |
| WO | WO 2003/094746 A1 | 11/2003 |
| WO | WO 2003/094747 A1 | 11/2003 |
| WO | WO 2003/079909 A3 | 3/2004 |
| WO | WO 2004/032763 A2 | 4/2004 |
| WO | WO 2007/127283 A2 | 11/2007 |
| WO | WO 2015/065485 A1 | 5/2015 |

OTHER PUBLICATIONS

U.S. Appl. No. 15/889,374, filed Feb. 6, 2018.
U.S. Appl. No. 15/889,376, filed Feb. 6, 2018.
U.S. Appl. No. 15/889,388, filed Feb. 6, 2018.
U.S. Appl. No. 15/889,390, filed Feb. 6, 2018.
European Search Report and Written Opinion dated Apr. 29, 2019 for Application No. EP 19155554.9, 13 pgs.
International Search Report and Written Opinion dated Apr. 29, 2019 for Application No. PCT/IB2010/050357, 20 pgs.

* cited by examiner

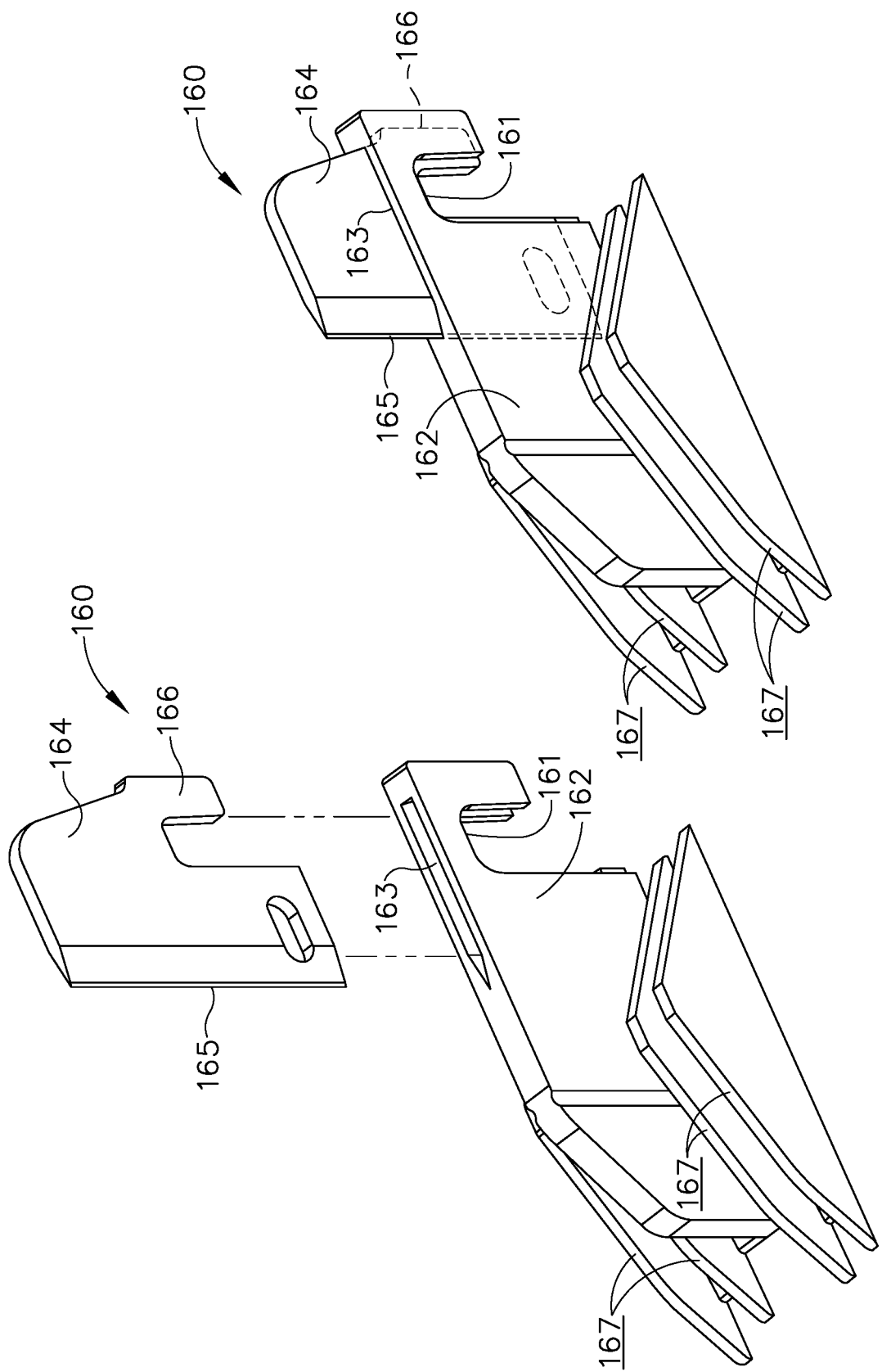

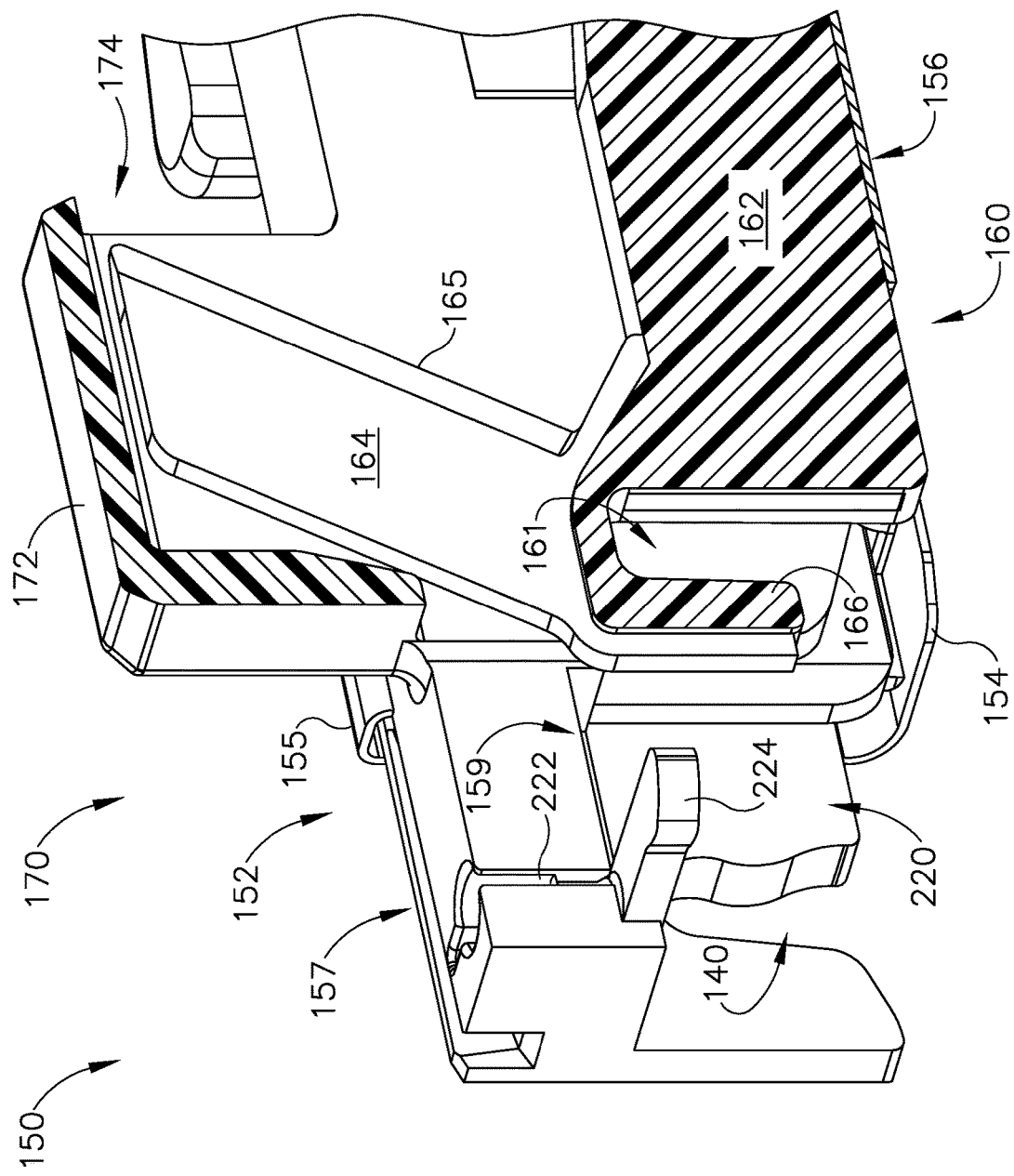

LOCKOUT ASSEMBLY FOR LINEAR SURGICAL STAPLER

BACKGROUND

In some surgical operations, such as a gastrointestinal anastomosis, it may be desirable to clamp down on one or more layers of tissue, cut through the clamped layers of tissue and drive staples through the layers of tissue to substantially seal the severed layers of tissue together near the severed ends of the tissue layers. One such instrument that may be used in such operations is a linear cutting stapler. A linear cutting stapler generally includes a first jaw, a second jaw, a lever for clamping the first jaw relative to the second jaw, an anvil associated with either the first jaw or the second jaw, a staple cartridge associated with the jaw opposing the staple anvil, and a firing assembly movable relative to the rest of the linear cutting stapler. The first jaw and the second jaw may pivot relative each other in order to grasp tissue between the jaws. Staples are arranged in the staple cartridge such that a portion of firing assembly may actuate through the staple cartridge to drive staples out of staple cartridge, through the tissue, and against anvil while also severing tissue captured between the staple cartridge and the staple anvil.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts an exploded view of a staple sled assembly of the surgical stapling instrument of FIG. 1;

FIG. 8 depicts a perspective view of the staple sled assembly of FIG. 7;

FIG. 12 depicts a cross-sectional perspective view of the staple cartridge assembly of FIG. 4, taken along line 12-12 of FIG. 5;

Figure 1:
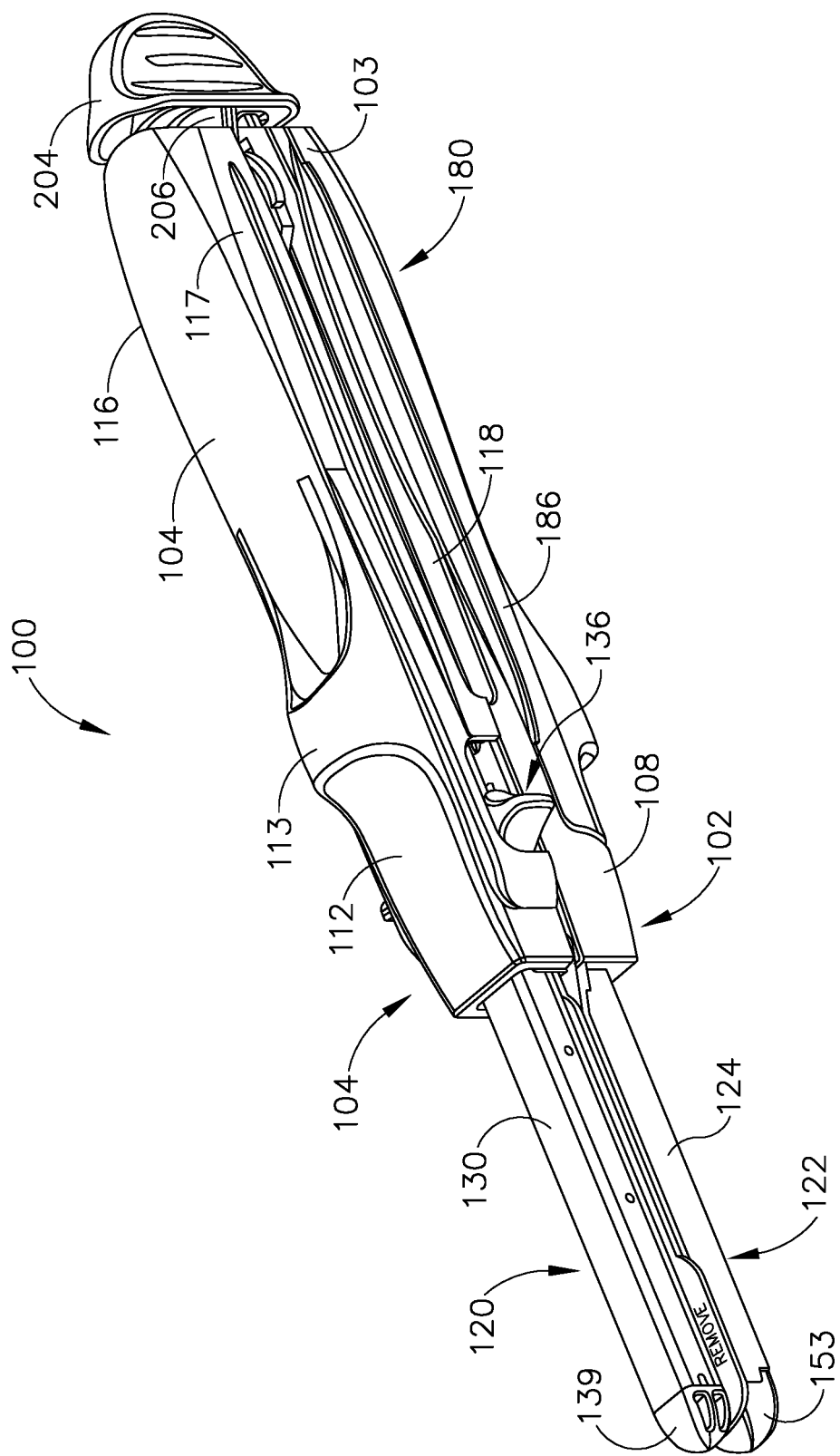
FIG. 1 depicts a perspective view of an exemplary surgical stapling instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

I. OVERVIEW OF EXEMPLARY LINEAR CUTTING STAPLER

FIG. 1 depicts an exemplary surgical linear cutting stapler (100) that may be used for any suitable procedure, such as a gastrointestinal anastomosis. Linear cutting stapler (100) includes a first portion (102) having a staple cartridge channel (122), a second portion (104) having an anvil channel (130), a staple cartridge assembly (150) that may selectively couple with cartridge channel (122) of first portion (102), and a firing assembly (200). As will be described in greater detail below, first portion (102) and staple cartridge assembly (150) may pivotably couple with second portion (104) to form an end effector (120) capable of clamping, severing, and stapling tissue captured between opposing halves of end effector (120).

As best seen in FIGS. 3-6, firing assembly (200) includes an actuating beam (202), a staple sled assembly (160) housed within staple cartridge assembly (150), an actuator (204) (also referred to as a "firing knob"), and a pivot arm (206). Actuating beam (202) extends from a distal end (201) to a proximal end (203). Actuating beam (202) is slidably housed within first portion (102). Pivot arm (206) connects actuator (204) with distal end (201) of actuating beam (202). Actuator (204) and pivot arm (206) may pivot from a proximal position (shown in FIG. 1) to either lateral side of actuating beam (202) (shown in FIG. 11A), thereby enabling an operator to actuate firing assembly (200) from either a first side (116) or a second side (117) of instrument (100) when portions (102, 104) are properly coupled and end effector (120) is in the fully closed position. It should be understood when instrument (100) is properly coupled and end effector (120) is in the fully closed position, first portion (102) and second portion (104) define a slot (118) dimensioned to accommodate translation of actuator (204). In the current example, as will be described in greater detail below, actuating beam (202) is operable to couple with staple sled assembly (160) when staple cartridge assembly (150) is suitably coupled with first portion (102) such that actuator (204) may slide along first side (116) or second side (117) of instrument (100), thereby driving actuating beam (202) and staple sled assembly (160) distally through cartridge assembly (150) to fire instrument (100).

While in the present example, actuator (204) is configured to pivot to either side (116, 117) of instrument (100) to drive actuating beam (202), this is merely optional, as actuator (204) may slidably couple with first portion (102) or second portion (104) through any means apparent to one having ordinary skill in the art in view of the teachings herein. In one example, actuator (204) may strictly associate with first side (116) or second side (117) such that actuator (204) may not pivot when end effector (120) is in the fully closed position. In another example, there may be an actuator (204) positioned on both first side (116) and second side (117), such that instrument (100) may include two actuators (204).

Figure 3:
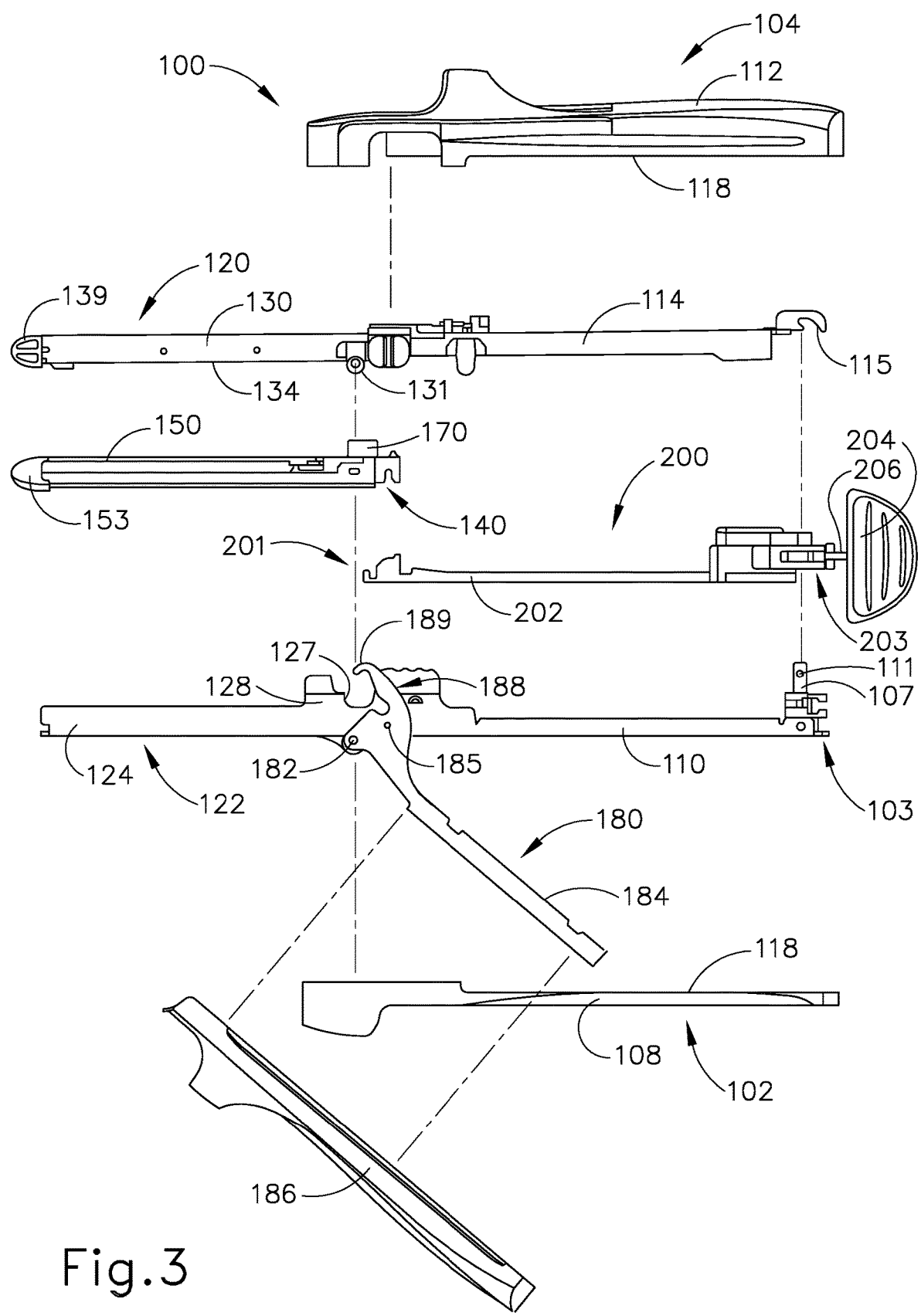
FIG. 3 depicts an exploded elevational side view of the surgical stapling instrument of FIG. 1.

As seen in FIG. 3, first portion (102) includes a first proximal frame (110), staple cartridge channel (122), and a latching lever (180). First proximal frame (110) extends from a proximal end (103) distally into staple cartridge channel (122). In the present example, first proximal frame (110) and staple cartridge channel (122) are formed integrally so as to define an elongate cartridge channel member having a unitary construction. Latching lever (180) is pivotably coupled to either staple cartridge channel (122) or first proximal frame (110) via a pin (182). First proximal frame (110) may be coupled with a handle cover (108) configured to promote sufficient grip such that an operator may control instrument (100) while the operator performs a suitable procedure. Handle cover (108) may couple with first proximal frame (110) by any suitable means as would be apparent to one having ordinary skill in the art in view of the teachings herein. Alternatively, handle cover (108) may be unitarily coupled with first proximal frame (110) or even omitted.

First proximal frame (110) defines a channel that slidably houses actuating beam (202) of firing assembly (200). Proximal end (103) includes one or more lateral pins, or projections (111). Projections (111) are configured to receive grooves (115) of second portion (104) in order to initially pivotably couple first and second portions (102, 104). In the current example, projections (111) are raised from the rest of first proximal frame (110) via a post (107), however this is merely optional. For instance, projections (111) may include a single pin extending laterally across side walls of first proximal frame (110). Of course, any suitable means of initially pivotably couplings first portion (102) and second portion (104) may be used as would be apparent to one having ordinary skill in the art in view of the teachings herein.

Figure 2:
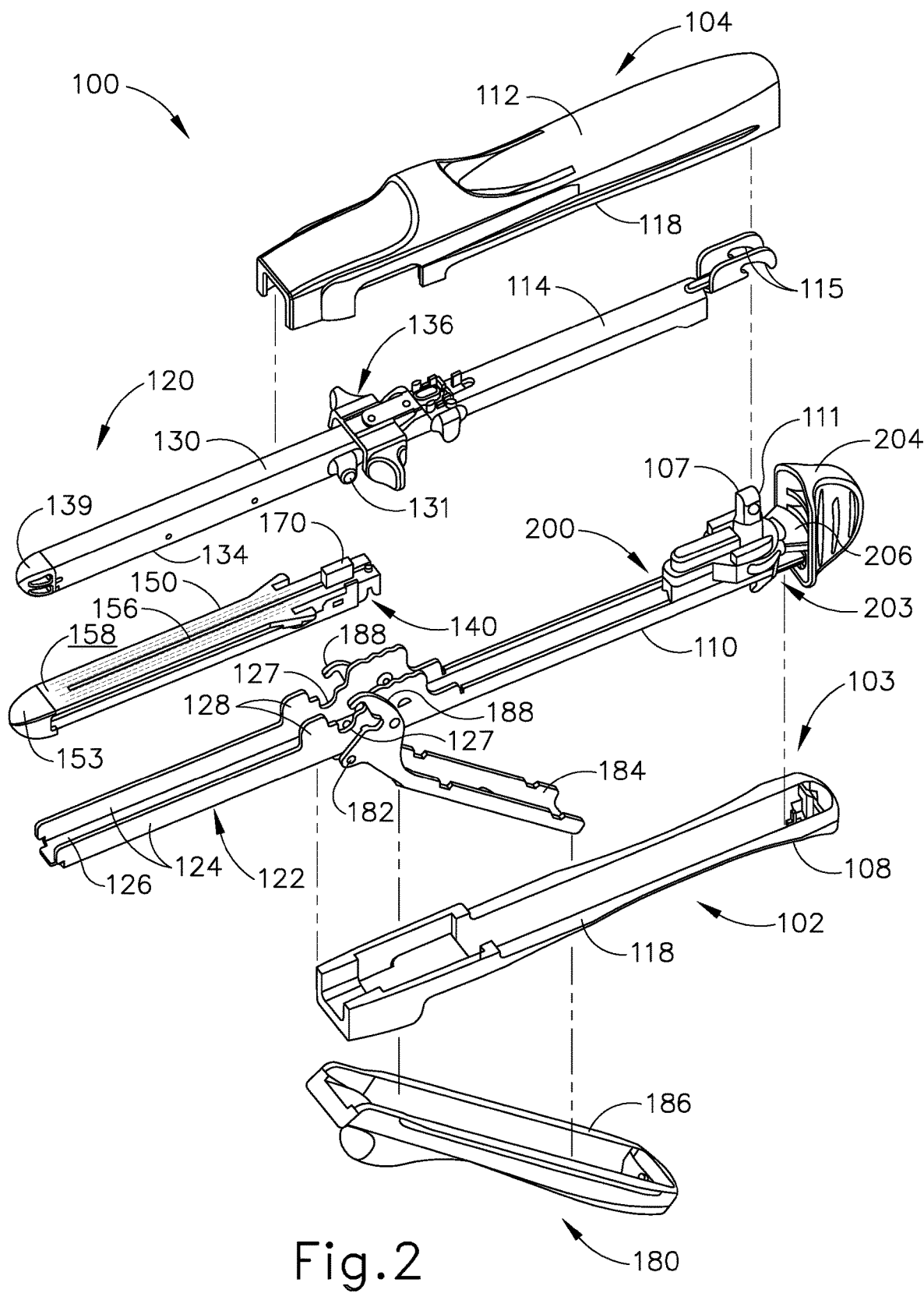
FIG. 2 depicts an exploded perspective view of the surgical stapling instrument of FIG. 1.
Figure 4:
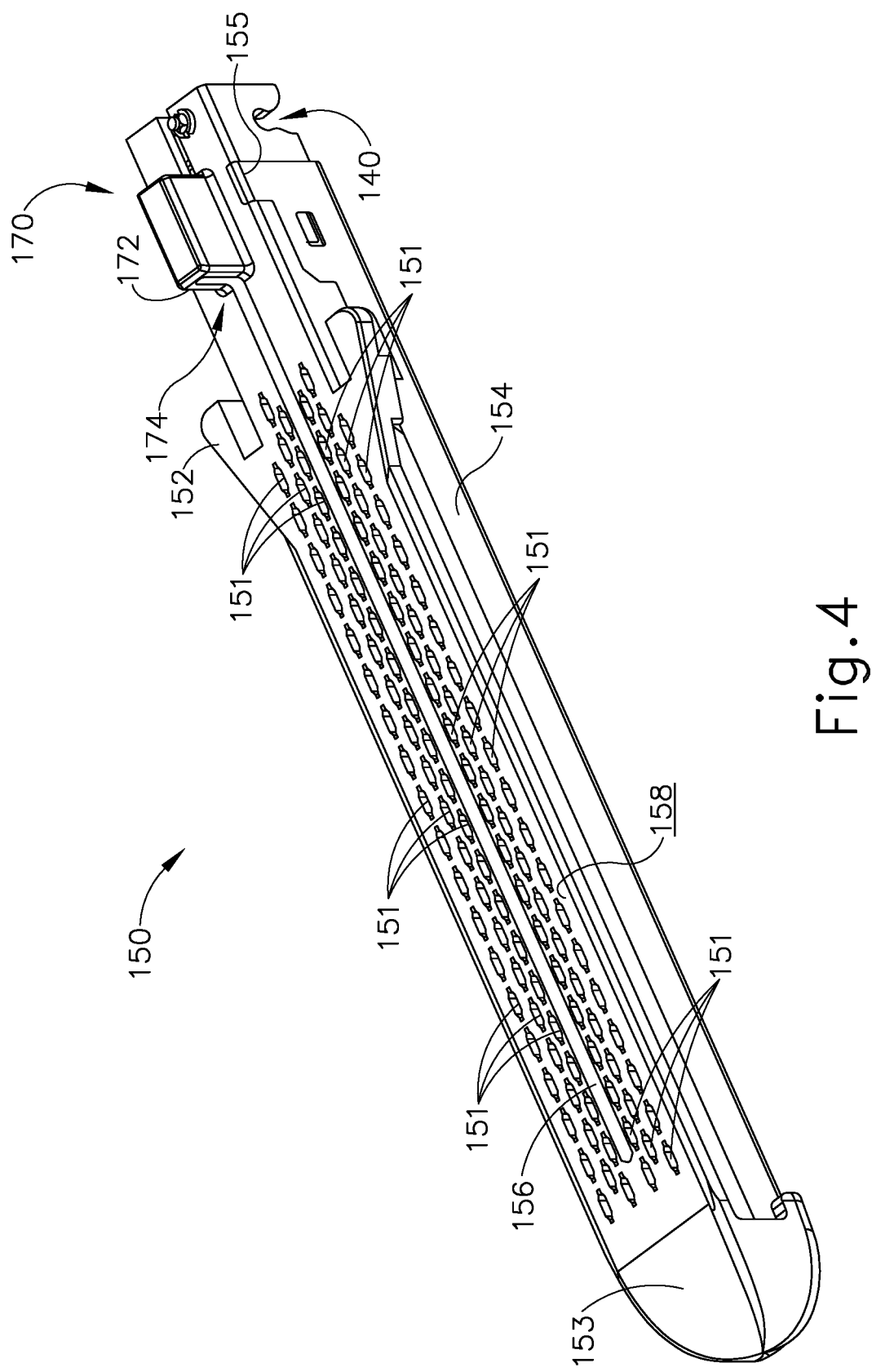
FIG. 4 depicts a perspective view of a staple cartridge assembly of the surgical stapling instrument of FIG. 1.

As briefly mentioned above, staple cartridge channel (122) extends distally from first proximal frame (110). As seen in FIG. 2, staple cartridge channel (122) is dimensioned to selectively couple and decouple with staple cartridge assembly (150). Staple cartridge channel (122) includes a bottom wall (126), and two opposed side walls (124) extending from opposite ends of bottom wall (126). Walls (124, 126) are dimensioned to receive at least a portion of staple cartridge assembly (150), as seen in FIG. 4. Additionally, side walls (124) include inwardly extending lateral projections (not shown) configured to receive coupling cutouts (140) defined by a proximal end of staple cartridge assembly (150). Coupling cutouts (140) may be dimensioned for a snap-fitting or press-fitting with inwardly extending lateral projections (not shown) of side walls (124) such that an operator may selectively attach and detach staple cartridge assembly (150) to staple cartridge channel (122). While coupling cutouts (140) and inwardly extending lateral projections (not shown) are used to selectively couple staple cartridge assembly (150) with staple cartridge channel (122), any other suitable coupling means may be used as would be apparent to one having ordinary skill in the art in view of the teachings herein. Side walls (124) of staple cartridge channel (122) also include side flanges (128) each defining a notch or recess (127). Recesses (127) are dimensioned to receive latch projections (131) of second portion (104) when second portion (104) pivots such that end effector (120) is in a fully closed position (as shown in FIG. 10D) relative to first portion (102).

As briefly mentioned above, latching lever (180) is pivotably coupled to the rest of first portion (102) via pivot pin (182). Latching lever (180) includes a proximal extending arm (184) and a distal latch body (188). Proximal extending arm (184) may be pivoted about pin (182) toward first proximal frame (110) in order to pivot distal latch body (188) toward staple cartridge channel (122) such that distal latch body (188) may engage and pivot second portion (104) toward first portion (102) to transition end effector (120) from a partially closed position (as shown in FIG. 10C) to a fully closed position (as shown in FIG. 10D).

Proximally extending arm (184) may be coupled with an arm cover (186) to promote sufficient grip such that an operator may grasp arm (184) while the operator performs a suitable procedure. Arm cover (186) may be coupled with proximal extending arm (184) by any suitable means as would be apparent to one having ordinary skill in the art in view of the teachings herein. Alternatively, arm cover (186) may be unitarily coupled with proximally extending arm (184) or even omitted.

Distal latch body (188) includes a pair of hooks (189). Distal latch body (188) also defines a corresponding pair of latch cutouts (185) located proximally relative to hooks (189). As will be described is greater detail below, each hook (189) is dimensioned to initially make contact with and then capture a respective latch projection (131) of second portion (104) such that distal latch body (188) may wrap around at least a portion of each latch projection (131) to further pivot second portion (104) toward first portion (102). As will also be described in greater detail below, each latch cutout (185) is dimensioned to receive a respective latch projection (131) when end effector (120) is in the closed position relative to first portion (102).

Figure 5:
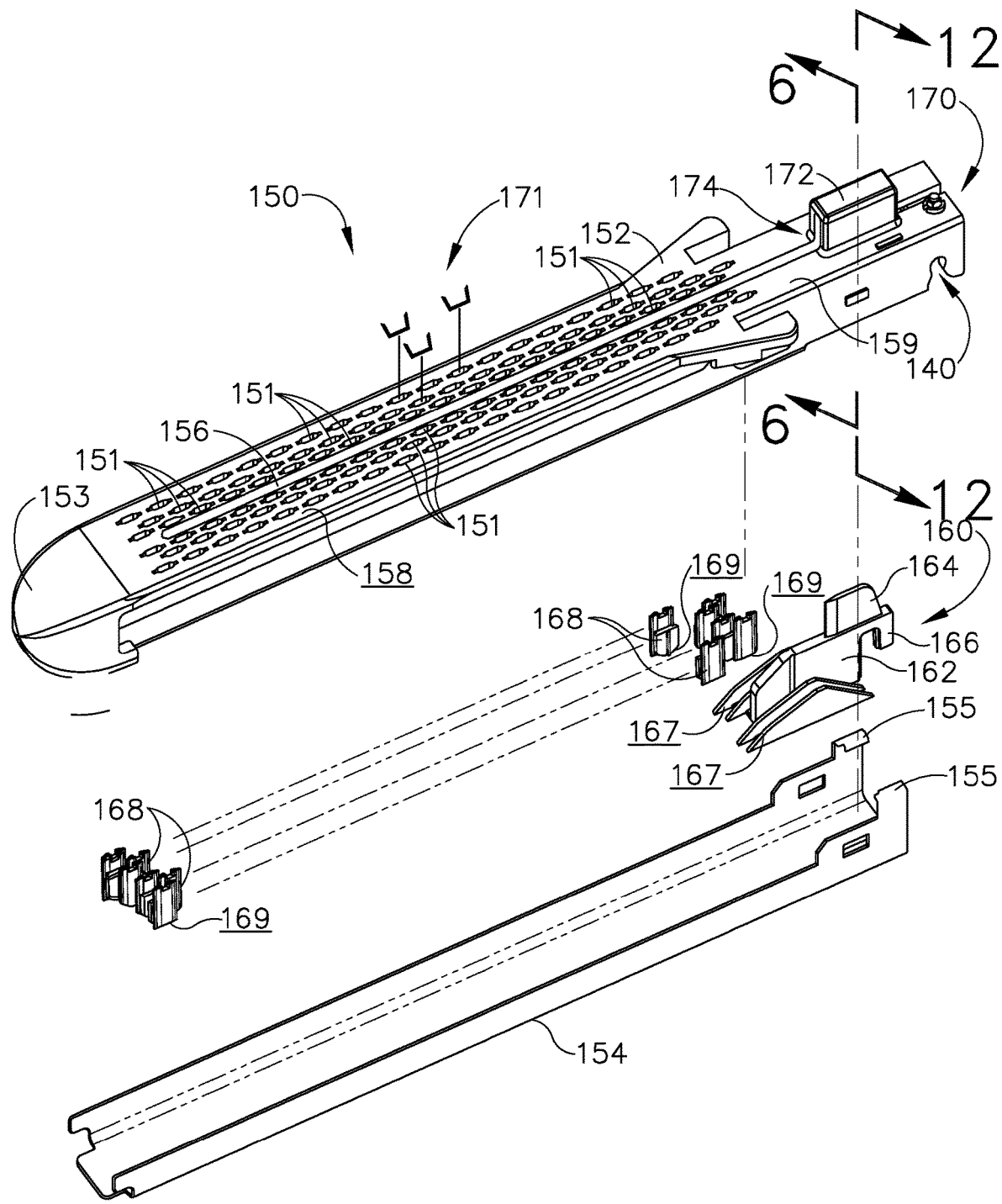
FIG. 5 depicts an exploded view of the staple cartridge assembly of FIG. 4.
Figure 6:
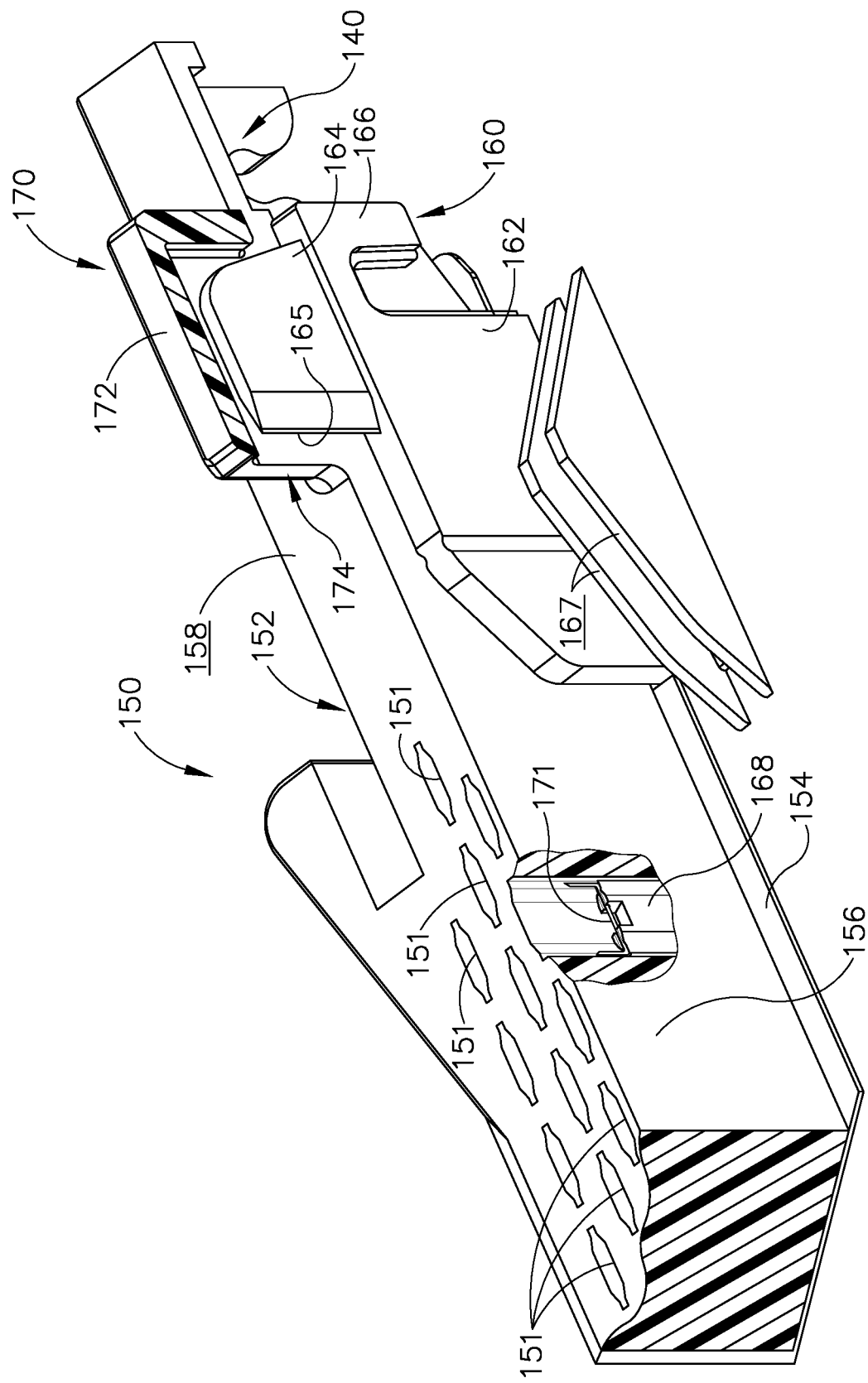
FIG. 6 depicts a cross-sectional perspective view of the staple cartridge assembly of FIG. 4, taken along line 6-6 of FIG. 5.

As best seen in FIGS. 4-6, staple cartridge assembly (150) includes a cartridge body (152), a pan (154), and a plurality of staple drivers (168), each configured to drive a respective staple (not shown). Cartridge body (152) defines a plurality of staple cavities (151), a slot (156), and coupling cutouts (140). Staple drivers (168) and respective staples (not shown) are slidably housed within a corresponding staple cavity (151). When first portion (102) and second portion (104) are coupled together, staple cartridge assembly (150) and staple cartridge channel (122) form a portion of end effector (120). As will be described in greater detail below, staple cartridge assembly (150) is configured to house or receive staple sled assembly (160) of firing assembly (200) such that staple sled assembly (160) may actuate through cartridge assembly (150) in order to simultaneously sever and staple tissue captured between the two halves of end effector (120).

As mentioned above, coupling cutouts (140) of cartridge body (152) may be dimensioned for a snap-fitting with inwardly extending lateral projections (not shown) of side walls (124) of staple cartridge channel (122) such that an operator may selectively attach and detach staple cartridge assembly (150) to staple cartridge channel (122). Cartridge body (152) includes a distal nose (153). When staple cartridge assembly (150) is properly coupled with cartridge channel (122), distal nose (153) may extend distally from cartridge channel (122) to provide an atraumatic tip.

Additionally, cartridge body (152) includes a staple deck (158). Staple deck (158) partially defines staple cavities (151) such that staple cavities (151) extend from an interior of cartridge body (152) toward an open end at staple deck (158). Staple cavities (151) each house a corresponding staple driver (168) and staple (not shown). Similarly, staple deck (158) partially defines slot (156) that extends from an interior of cartridge body (152) toward an open end at staple deck (158). Slot (156) is dimensioned to slidably receive a portion of a sled body (162) and cutting member (164) of staple sled assembly (160) such that cutting member (164) may sever tissue as staple sled assembly (160) slides distally through cartridge body (152).

Pan (154) may include flexible arms (155). Flexible arms (155) may be configured to engage cartridge body (152) such that pan (154) may couple with cartridge body (152) in a snap-fit or press-fit relationship. Pan (154) may couple with cartridge body (152) after staple drivers (168) and staples (not shown) have been inserted into respective staple cavities (151). Pan (154) may therefore act as a floor for staple drivers (168).

In the current example, cartridge body (152) includes a sled assembly housing (170) located near the proximal end of staple cartridge assembly (150). Sled assembly housing (170) is configured to initially house staple sled assembly (160) of firing assembly (200). Sled assembly housing (170) includes a body (172) defining a cavity (174) having a distally facing opening. Body (172) and cavity (174) are dimensioned to house a cutting member (164) of sled assembly (160) prior to firing, therefore acting as a sheath for cutting member (164). When fired, cutting member (164) may exit sled assembly housing (170) via the distally facing opening of cavity (174).

As seen best in FIGS. 7 and 8, sled assembly (160) includes a sled body (162) and a cutting member (164). Cutting member (164) includes a cutting edge (165) and a lock arm (166). Sled body (162) defines a cutout (161) and a slot (163). Slot (163) is dimensioned to receive a portion of cutting member (164) such that cutting member (164) and sled body (162) may actuate together. Cutting member (164) may couple with sled body (162) via an inference fit with slot (163), through use of adhesives, or any other suitable manner as would be apparent to one having ordinary skill in the art in view of the teachings herein. Alternatively, cutting member (164) may couple with sled body (162) though any suitable manner as would be apparent to one having ordinary skill in the art in view of the teachings herein, such as being unitarily connected, welding, etc. Cutout (161) is dimensioned to couple with distal end (201) of actuating beam (202) when staple cartridge assembly (150) is properly attached to staple cartridge channel (122). Therefore, when properly coupled, actuating beam (202) may drive sled assembly (160) longitudinally through cartridge body (152). It should be understood that since actuating beam (202) is coupled with sled assembly (160) during exemplary use, actuating beam (202) is also dimensioned to slide within slot (156) defined by cartridge body (152).

Sled body (162) also includes a plurality of cam surfaces (167) dimensioned to slide longitudinally within respective elongate grooves (not shown) that pass through staple cavities (151) of cartridge body (152). In particular, cam surfaces (167) are configured to engage and cam against sloped surfaces (169) of staple drivers (168) within staple cavities (151) in order to actuate staple drivers (168) toward staple deck (158). Staple drivers (168) then drive corresponding staples (not shown) through staple cavities (151) away from staple deck (158).

As mentioned above, staple sled assembly (160) is configured to couple with the rest of firing assembly (200) when staple cartridge assembly (150) is suitably coupled with staple cartridge channel (122). In the current example, staple sled assembly (160) of firing assembly (200) is associated with cartridge assembly (150) such that after cartridge assembly (150) is used and disposed of, so is staple sled assembly (160). Therefore, when an additional cartridge assembly (150) is loaded into staple cartridge channel (122), a new staple sled assembly (160) will be present. However, this is merely optional. For instance, staple sled assembly (160) may be fixed or otherwise coupled to the rest of firing assembly (200) such that the same staple sled assembly (160) may be used multiple times with multiple staple cartridge assemblies (150). In such examples, cartridge body (152) would not need a sled assembly housing (170). Various ways in which staple sled assembly (160) may be incorporated into either staple cartridge assembly (150), staple cartridge channel (122), or first proximal frame (110) will be apparent to one having ordinary skill in the art in view of the teachings herein.

As shown in FIGS. 2 and 3, second portion (104) of instrument (100) includes a second proximal frame (114), anvil channel (130), latch projections (131), and an anvil plate (134). Second proximal frame (114) extends from a proximal end defining grooves (115) in anvil channel (130). In the present example, second proximal frame (114) and anvil channel (130) are formed integrally so as to define an elongate anvil channel member having a unitary construction. Second proximal frame (114) may be coupled with a handle cover (112) configured to promote sufficient grip such that an operator may control instrument (100) while the operator performs a suitable procedure. Handle cover (112) and second proximal frame (114) may couple with each other by any suitable means as would be apparent to one having ordinary skill in the art in view of the teachings herein. Alternatively, handle cover (112) may be unitarily coupled with second proximal frame (114) or even omitted. Second proximal frame (114) may also define a channel configured to enable portions of firing assembly (200) to actuate relative to first portion (102) and second portion (104) when end effector (120) is in the fully closed position (as shown in FIG. 10D).

Figure 9:
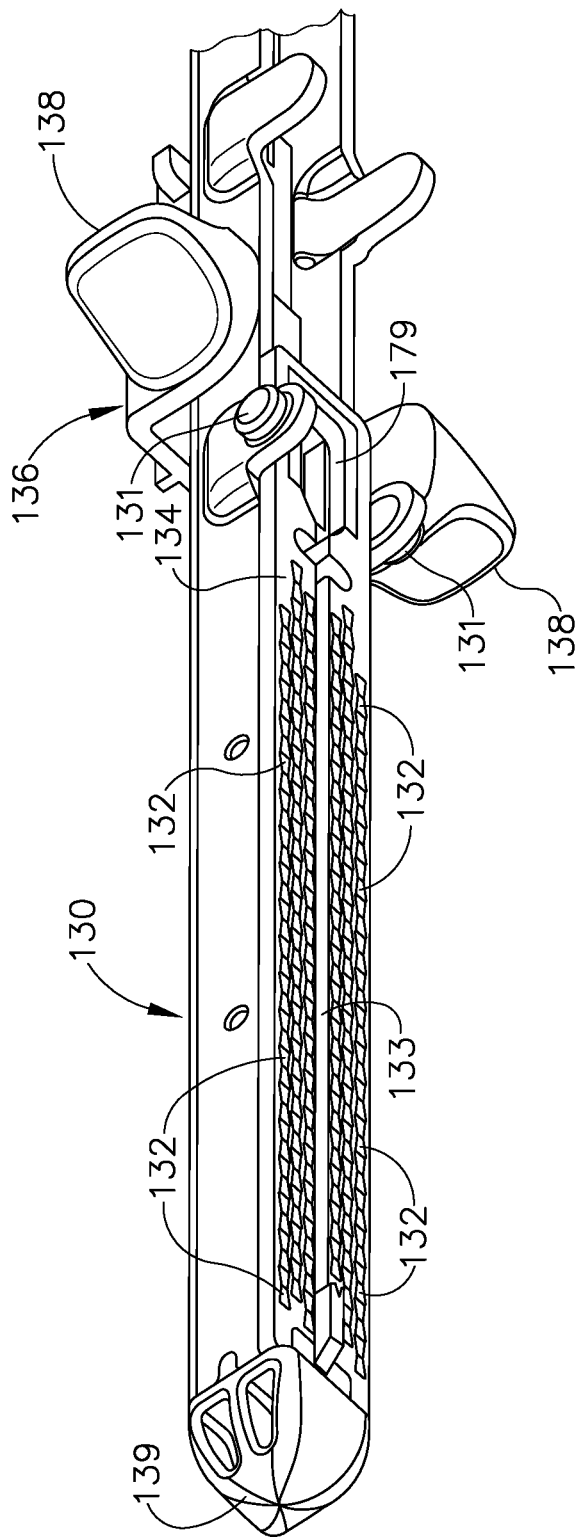
FIG. 9 depicts a perspective view of an anvil assembly of the surgical stapling instrument of FIG. 1.

Second portion (104) terminates distally in a distal nose (139). Distal nose (139) may extend distally from anvil channel (130) to provide an atraumatic tip. As shown in FIG. 9, proximal end of anvil plate (134) defines a recess (179) dimensioned to receive sled assembly housing (170) when first portion (102) and second portion (104) are pivoted toward each other. As will be described in greater detail below, latch projections (131) extend laterally away from anvil channel (130) and are dimensioned to interact with distal latch body (180) to draw anvil plate (134) toward staple cartridge assembly (150).

Anvil plate (134) defines a plurality of staple forming pockets (132) and a slot (133). Staple forming pockets (132) are positioned along anvil plate (134) such that each staple forming pocket (132) aligns with a corresponding staple cavity (151) when anvil channel (130) is pivoted toward staple cartridge channel (122) to the fully closed position (as shown in FIGS. 1, 10D, and 11A-B). Therefore, when cam surfaces (167) of sled body (162) actuate staple drivers (168) in accordance with the description above, staples (not shown) are driven through staple cavities (151) away from staple deck (158), through tissue, and against a corresponding staple forming pocket (132) such that staples (not shown) transform from a general "U" shape into a general "B" shape in order to suitably staple tissue. Slot (133) is dimensioned to laterally align with slot (156) of staple cartridge assembly (150) when anvil channel (130) is pivoted to the fully closed position (as shown in FIGS. 1, 10D, 11A-11B). Slot (133) is dimensioned to slidably receive a portion of cutting member (164) as staple sled assembly (160) is driven through staple cartridge assembly (150) such that cutting member (164) may sever tissue captured between anvil surface (134) and staple deck (158) during exemplary use.

As seen best in FIG. 9, second portion (104) of instrument (100) of the present example further includes a staple height adjustment mechanism (136). Adjustment mechanism (136) is operatively coupled with anvil plate (134), for example via one or more camming features (not shown), and includes a pair of user-engageable projections (138). Adjustment mechanism (136) is selectively movable relative to anvil channel (130) between two or more longitudinal positions to raise or lower anvil plate (134) relative to anvil channel (130), and thereby adjust a gap distance (or "tissue gap") between anvil plate (134) and staple deck (158) when first and second instrument portions (102, 104) are coupled together in a fully closed position. A larger gap distance, and thus a greater staple height, may be provided for stapling tissues of greater thicknesses. Similarly, a smaller gap distance, and thus a smaller staple height, may be provided for stapling tissues of lesser thicknesses. It will be appreciated that staple height adjustment mechanism (136) is merely optional and may be omitted in other examples.

Surgical linear cutting stapler (100) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and U.S. Pat. No. 8,789,740, entitled "Linear Cutting and Stapling Device with Selectively Disengageable Cutting Member," issued Jul. 29, 2014. The disclosure of each of these references is incorporated by reference herein.

Figure 10A:
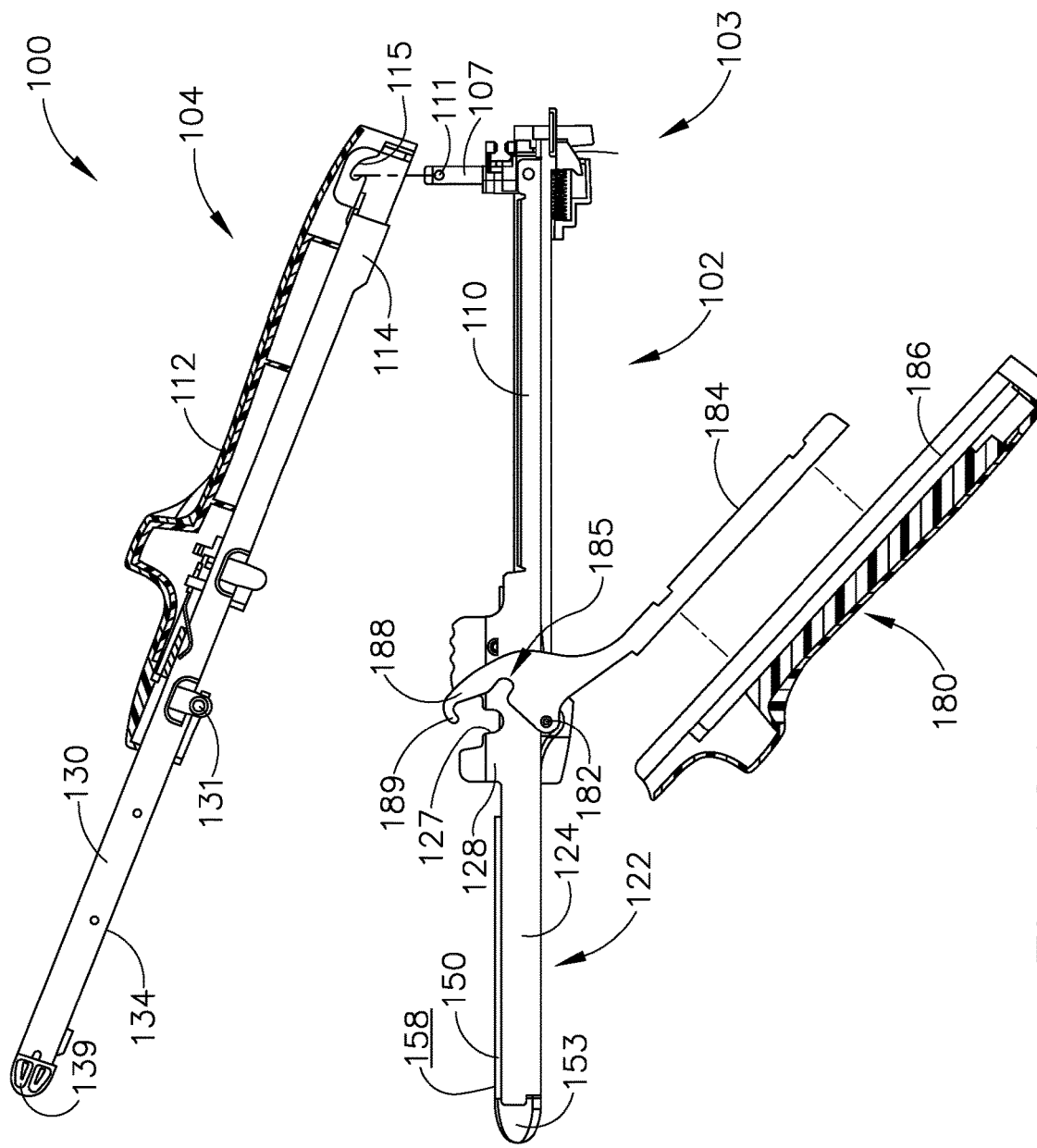
FIG. 10A depicts a cross-sectional side view of the surgical stapling instrument of FIG. 1, where a first portion and a second portion are decoupled from each other, and where an arm cover of the second portion is shown detached from the first portion for illustrative purposes.
Figure 10B:
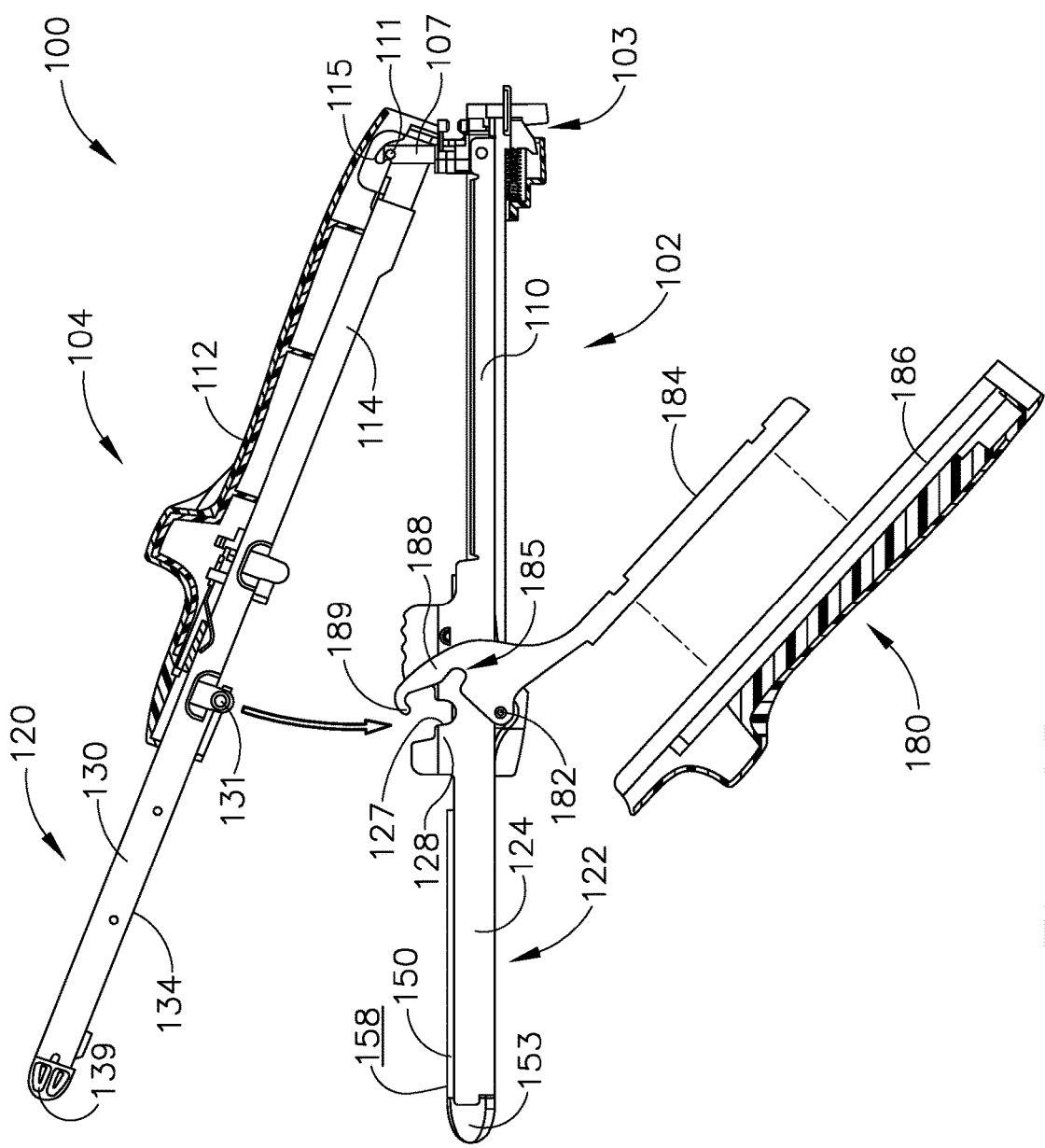
FIG. 10B depicts a cross-sectional side view of the surgical instrument of FIG. 1, where the first portion and the second portion of FIG. 10A are coupled with each other in an opened position.
Figure 10C:
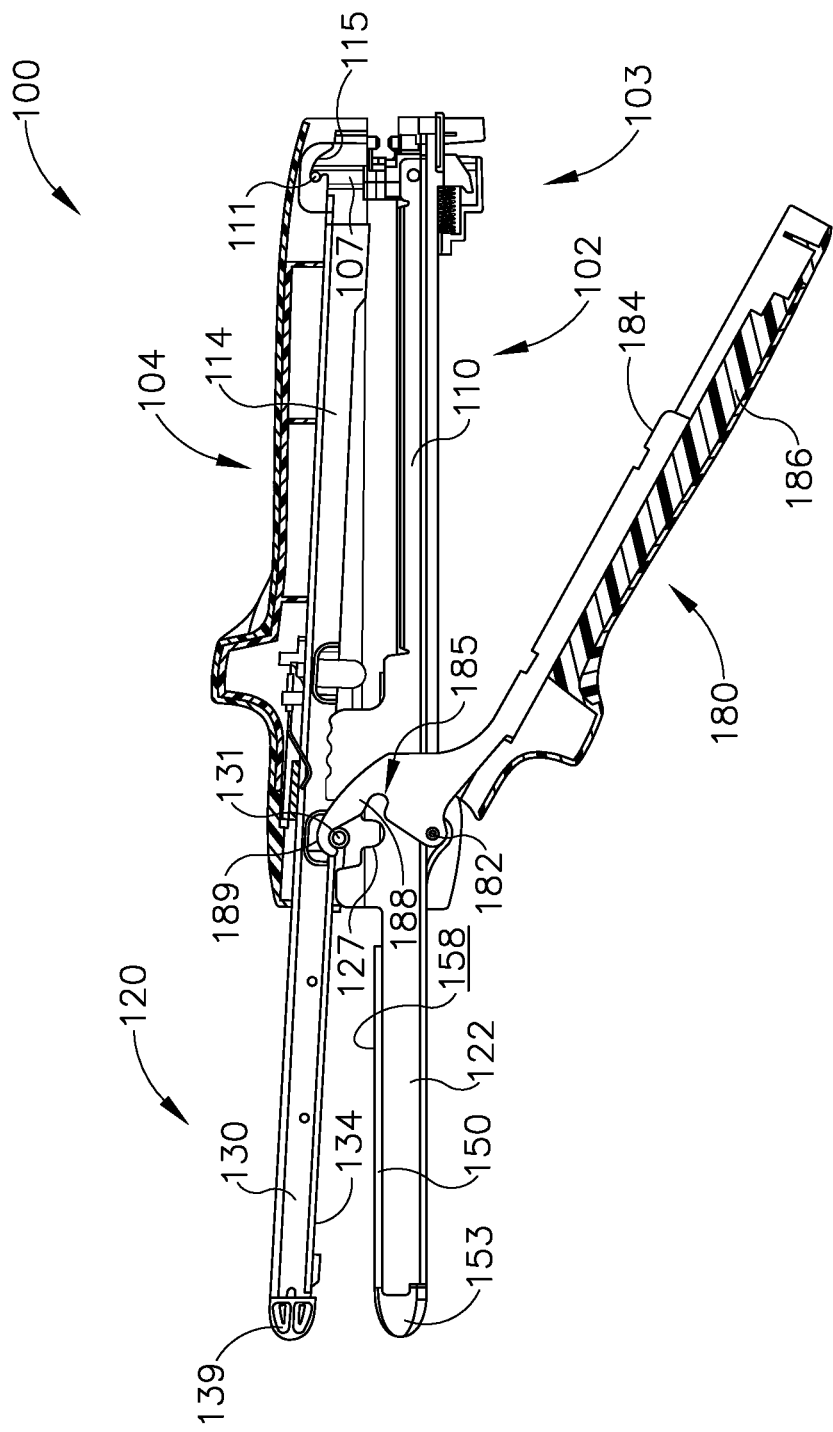
FIG. 10C depicts a cross-sectional side view of the surgical instrument of FIG. 1, where the first portion and the second portion of FIG. 10A are coupled with each other in a partially closed position.
Figure 10D:
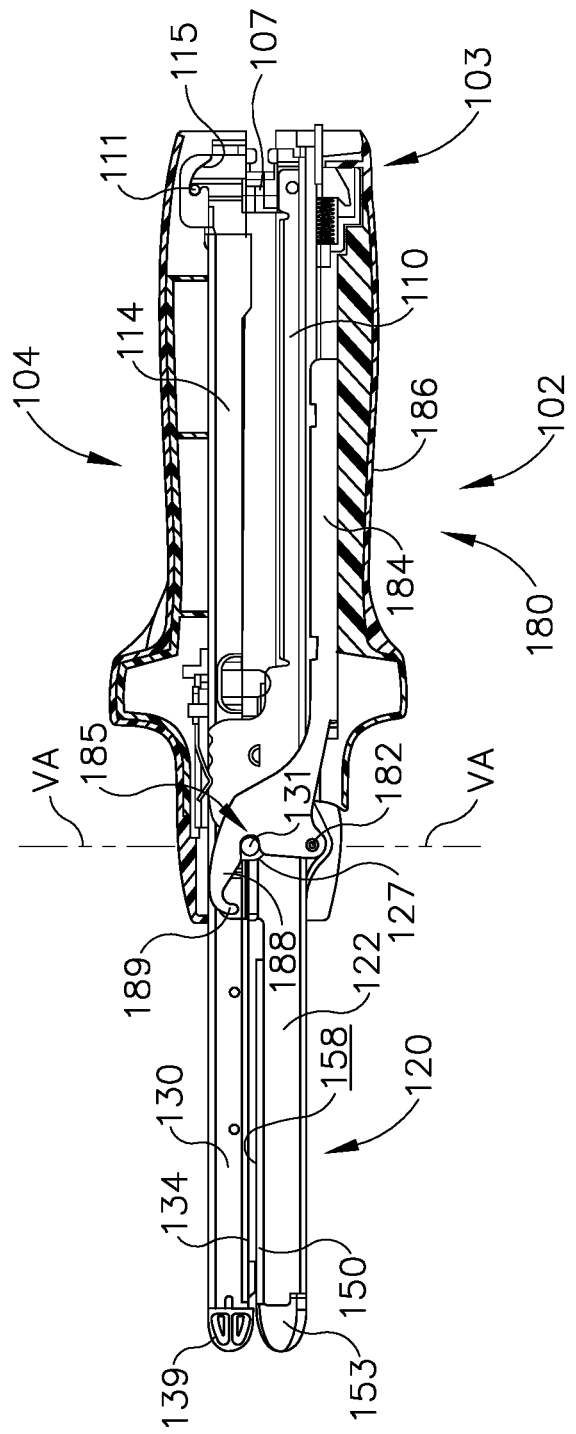
FIG. 10D depicts a cross-sectional side view of the surgical instrument of FIG. 1, where the first portion and the second portion of FIG. 10A are coupled with each other in a fully closed position.
Figure 11A:
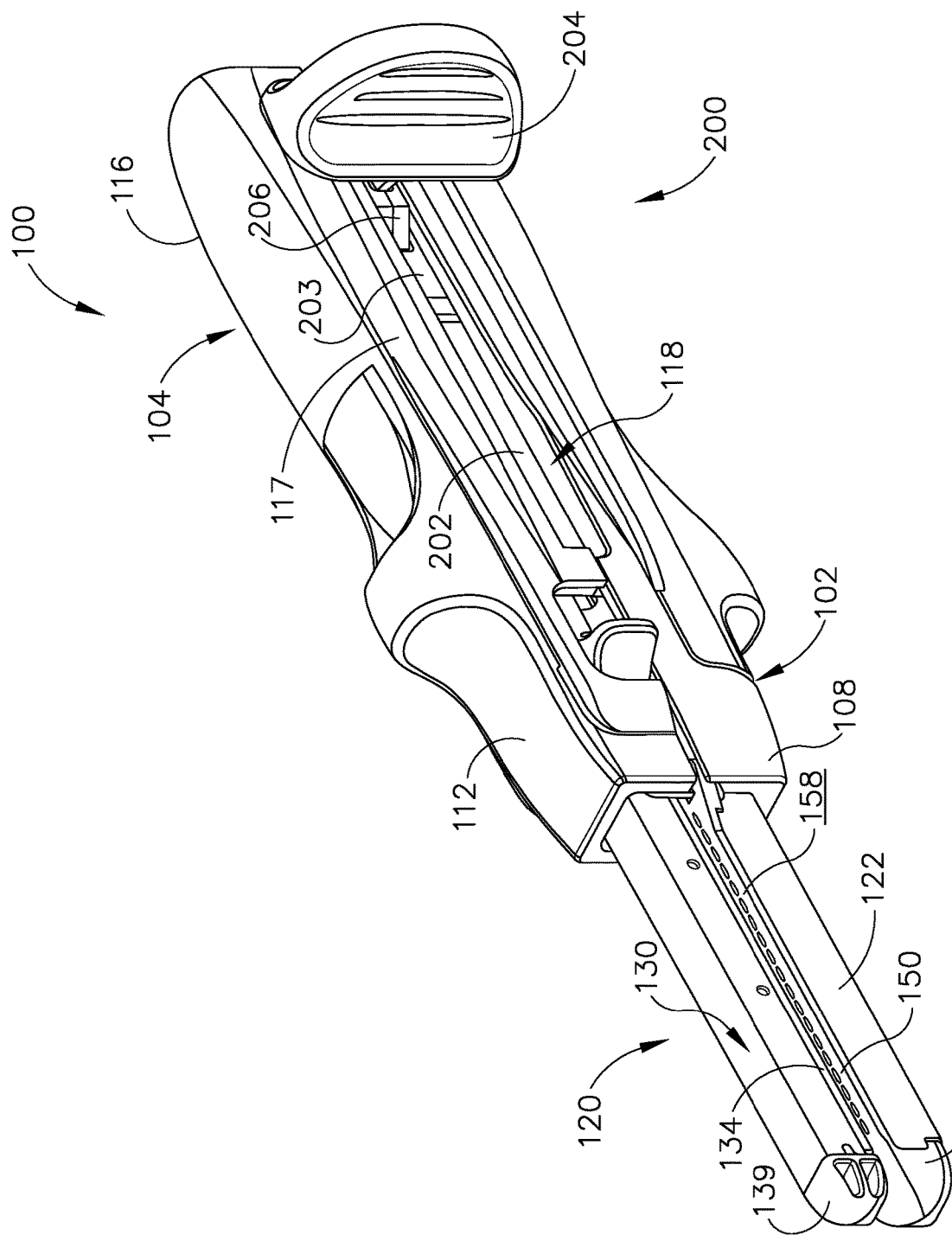
FIG. 11A depicts a perspective view of the surgical instrument of FIG. 1, where a firing assembly is in a pre-fired position.
Figure 11B:
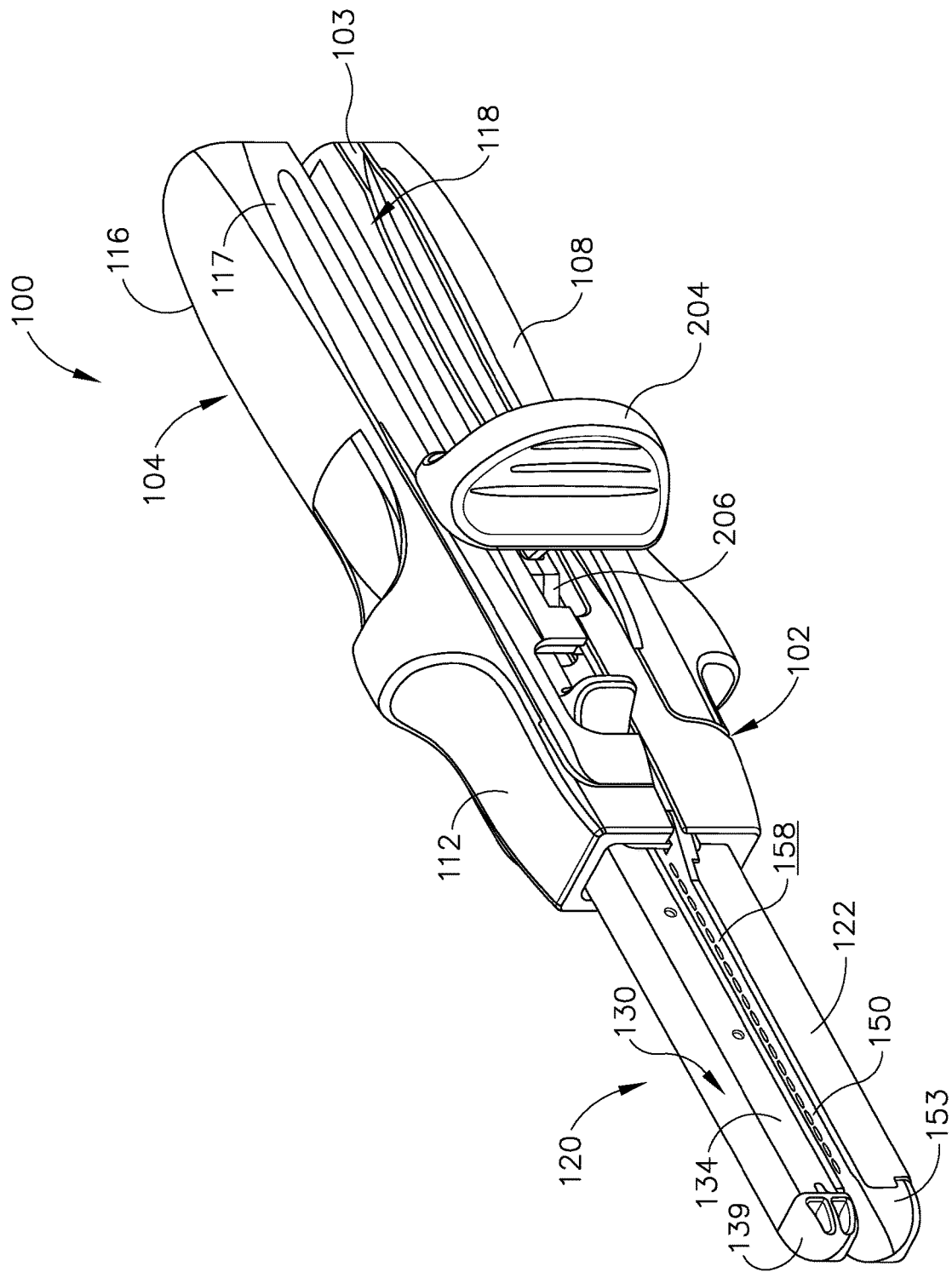
FIG. 11B depicts a perspective view of the surgical instrument of FIG. 1, where the firing assembly of FIG. 11A is in a fired position.

FIGS. 10A-11B show an exemplary use of instrument (100). In particular, FIGS. 10A-10D show an exemplary coupling of first portion (102) with second portion (104), and pivoting first portion (102) and second portion (104) such that end effector (120) transitions from an open position (FIG. 10B), to a partially closed position (FIG. 10C), and finally to a fully closed position (FIG. 10D). FIGS. 11A-11B show an exemplary firing of instrument (100) when end effector (120) is in a fully closed position.

FIG. 10A shows first portion (102) completely detached from second portion (204). Additionally, staple cartridge assembly (150) is suitably attached to staple cartridge channel (122) in accordance with the description above. At this point during a procedure, such as during a gastrointestinal anastomosis, an operator may desire to place lumens of tissue over and past distal noses (139, 153) of second portion (104) and cartridge assembly (150), respectively, such that lumens of tissue are suitably associated with both anvil plate (134) and cartridge assembly (150). At this point, an operator may align grooves (115) of second portion (104) with corresponding lateral projections (111) of first portion (102) in preparation of initially pivotally coupling first portion (102) with second portion (104).

Next, as shown in FIG. 10B, an operator may insert lateral projections (111) into corresponding grooves (115) such that first portion (102) and second portion (104) are pivotally coupled, but end effector (120) is in an open position. First portion (102) and second portion (104) may pivot relative to each other about the axis defined by lateral projections (111). At this point, latching lever (180) is not in contact with any portion of second portion (104). Additionally, latching lever (180) is in an open position such that proximal extending arm (184) is pivoted away from first proximal frame (110).

Next, as shown in FIG. 10C, an operator may initially pivot anvil channel (130) and anvil plate (134) toward cartridge channel (122) and staple cartridge assembly (150), and partially pivot latching lever (180) such that hooks (189) initially contact latch projections (131). At this point, end effector (120) is in the partially closed position. As best shown between FIGS. 10C-10D, after hooks (189) initially contact latch projections (131), an operator may further rotate proximal extending arm (184) toward first proximal frame (110), causing distal latch body (188) to drive latch projections (131) along the surfaces of distal latch body (188) toward latch cutouts (185). As latch projections (131) are driven toward latch cutouts (185), anvil channel (130) and anvil plate (134) rotate further toward cartridge channel (122) and staple cartridge assembly (150) such that end effector (120) is in the closed position. Additionally, latch projections (131) are also driven toward recesses (127) of staple cartridge channel (122) such that each latch projection (131) is encompassed by a combination of the respective latch cutout (185) and recess (127), effectively latching end effector (120) into the closed position. Latch cutouts (185) and recesses (127) may be dimensioned to interface with latch projections (131) while end effector (120) is in the fully closed position such that latch projections (131) and pivot pin (182) extend along a vertical axis (VA) that is substantially perpendicular with the longitudinal axis of instrument (100). This may provide a mechanical advantage for an enhanced closure force during suitable use.

FIGS. 11A-11B show an exemplary firing of instrument (100) with end effector (120) in the fully closed position. As best seen in FIG. 11A, an operator may pivot actuator (204) to either side (116, 117) of instrument (100). In the present example, actuator (204) has been pivoted to second side (117) of instrument (100). Next, operator may push actuator (204) distally toward end effector (120) within slot (118), such that actuating beam (202) and sled (160) are fired, thereby stapling and severing tissue captured between stapling deck (158) and anvil plate (134) in accordance with the description above. Once instrument (100) has been fired, an operator may pull actuator (204) proximally back to the position shown in FIG. 11A, then rotate actuator (204) back to the position shown in FIG. 1. An operator may then pivot latching lever (180) such that proximally extending arm (184) is pivoted away from first proximal frame (110) in order to open end effector (120) from the fully closed position to the partially closed position. An operator may further pivot latching lever (180) such that distal latch body (188) no longer captures latch projections (131). Then an operator may decouple first portion (102) and second portion (104) from each other and replace staple cartridge assembly (150), if desired.

It may be desirable to have a lockout assembly configured to prevent the firing of actuating beam (202) prior to loading staple cartridge assembly (150) into staple cartridge channel (122). Additionally, it may be desirable to have a lockout assembly configured to prevent multiple firings of actuating beam (202) within a single staple cartridge assembly (150). A lockout assembly configured to prevent premature firing of actuating beam (202) may reduce inadvertent and/or multiple firings of firing assembly (200) such that an operator does not mistakenly fire a cartridge assembly (150) with staples already deployed. A lockout assembly may also help ensure staple cartridge assembly (150) is suitably loaded into staple cartridge channel (122) prior to exemplary use.

Figure 14A:
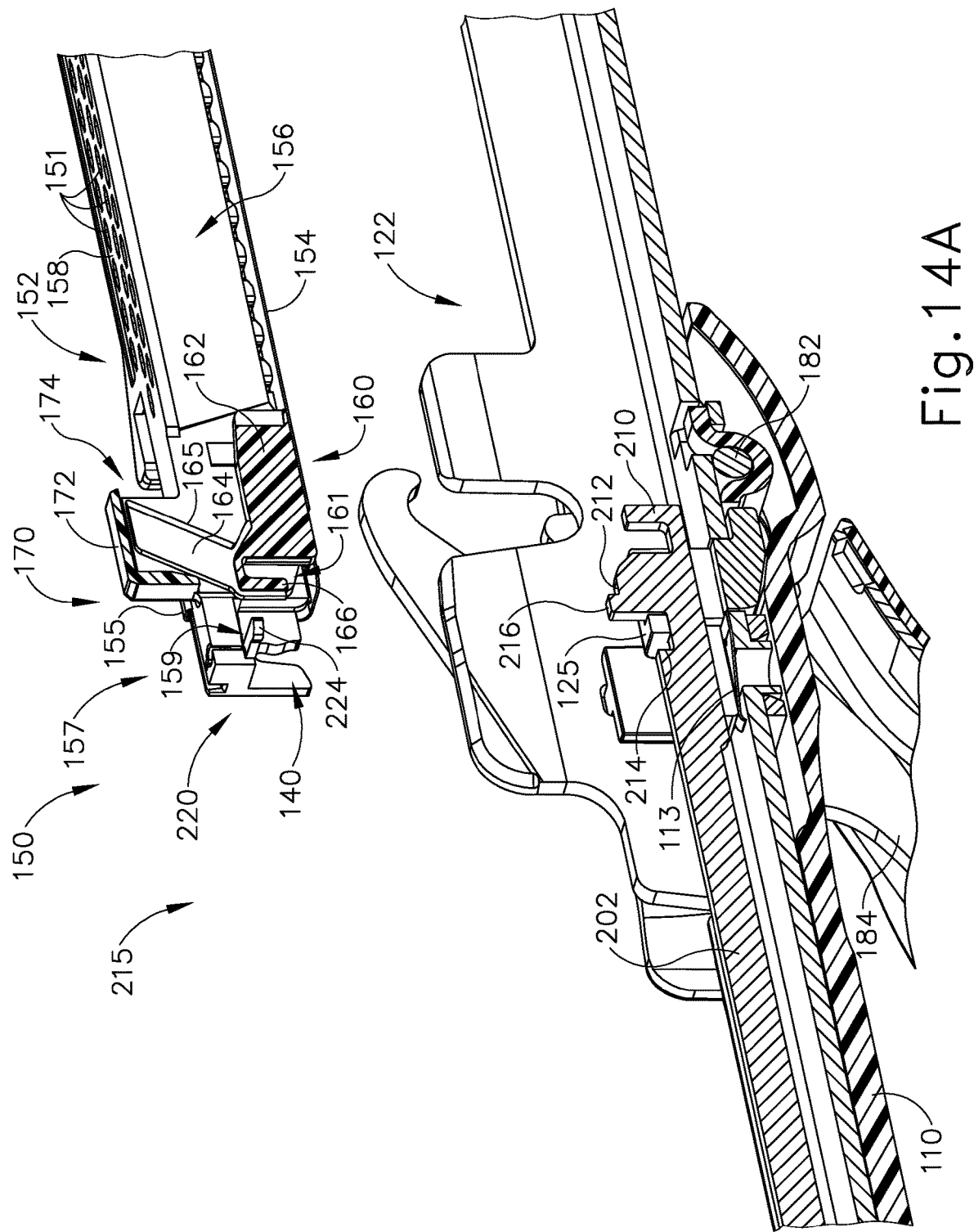
FIG. 14A depicts a cross-sectional perspective view of the staple cartridge assembly of FIG. 4 aligned for coupling with the first portion of FIG. 10A, where the firing assembly of FIG. 11A is in a locked-out configuration, taken along line 12-12 of FIG. 5.

FIGS. 14A-15D show an exemplary lockout assembly (215) configured to lockout firing assembly (200) prior to staple cartridge assembly (150) being suitably loaded into cartridge channel (122). Additionally, lockout assembly (215) is configured to lockout firing assembly (200) after actuating beam (202) and staple sled assembly (160) have been fired within staple cartridge assembly (150). Lockout assembly (215) includes a lockout swing gate (220) pivotably coupled with a proximal end of cartridge body (152), a lockout block (125) fixed within staple cartridge channel (122), and a leaf spring (113) within staple cartridge channel (122). As will be described in greater detail below, leaf spring (113) is configured to bias actuating beam (202) into engagement with lockout block (125) when actuating beam (202) is in the proximal position (as seen in FIG. 14A), thereby urging actuating beam (202) into a locked configuration.

Figure 14B:
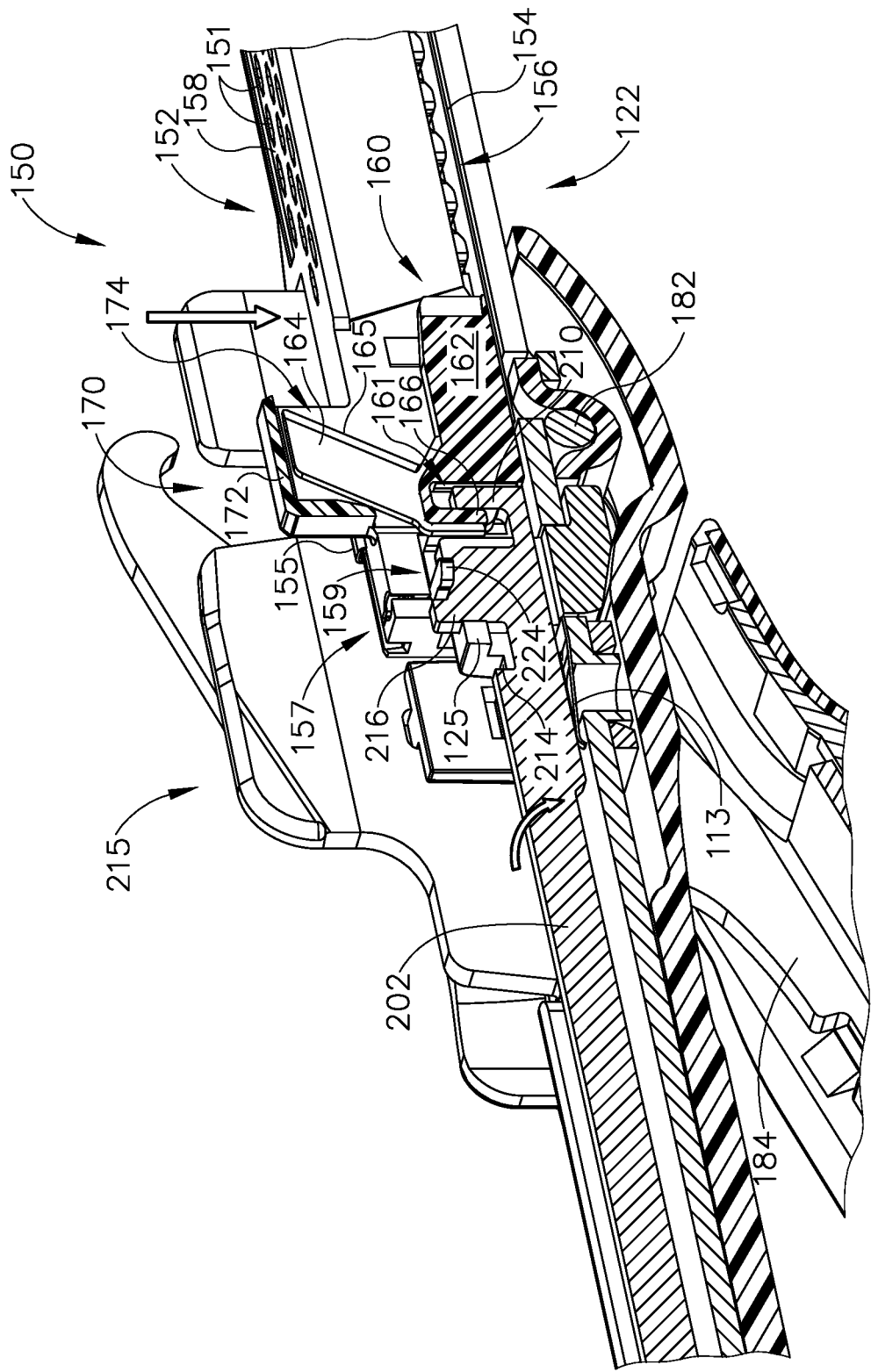
FIG. 14B depicts a cross-sectional perspective view of the staple cartridge assembly of FIG. 4 coupled with the first portion of FIG. 10A, where the firing assembly of FIG. 11A is in an unlocked configuration, taken along line 12-12 of FIG. 5.

Lockout swing gate (220) is configured to engage actuating beam (202) to force actuating beam (402) out of engagement with lockout block (125), and into an unlocked configuration, when staple cartridge assembly (150) is suitably loaded into staple cartridge channel (122) and actuating beam (202) is in the pre-fired proximal position (as seen in FIG. 14B). Additionally, as will be described in greater detail below, lockout swing gate (220) is also configured to pivot out of engagement with actuating beam (202) during actuation of firing assembly (200) such that lockout swing gate (220) is prevented from further engaging actuating beam (202) after firing assembly (200) is actuated distally in accordance with the description above.

Figure 13:
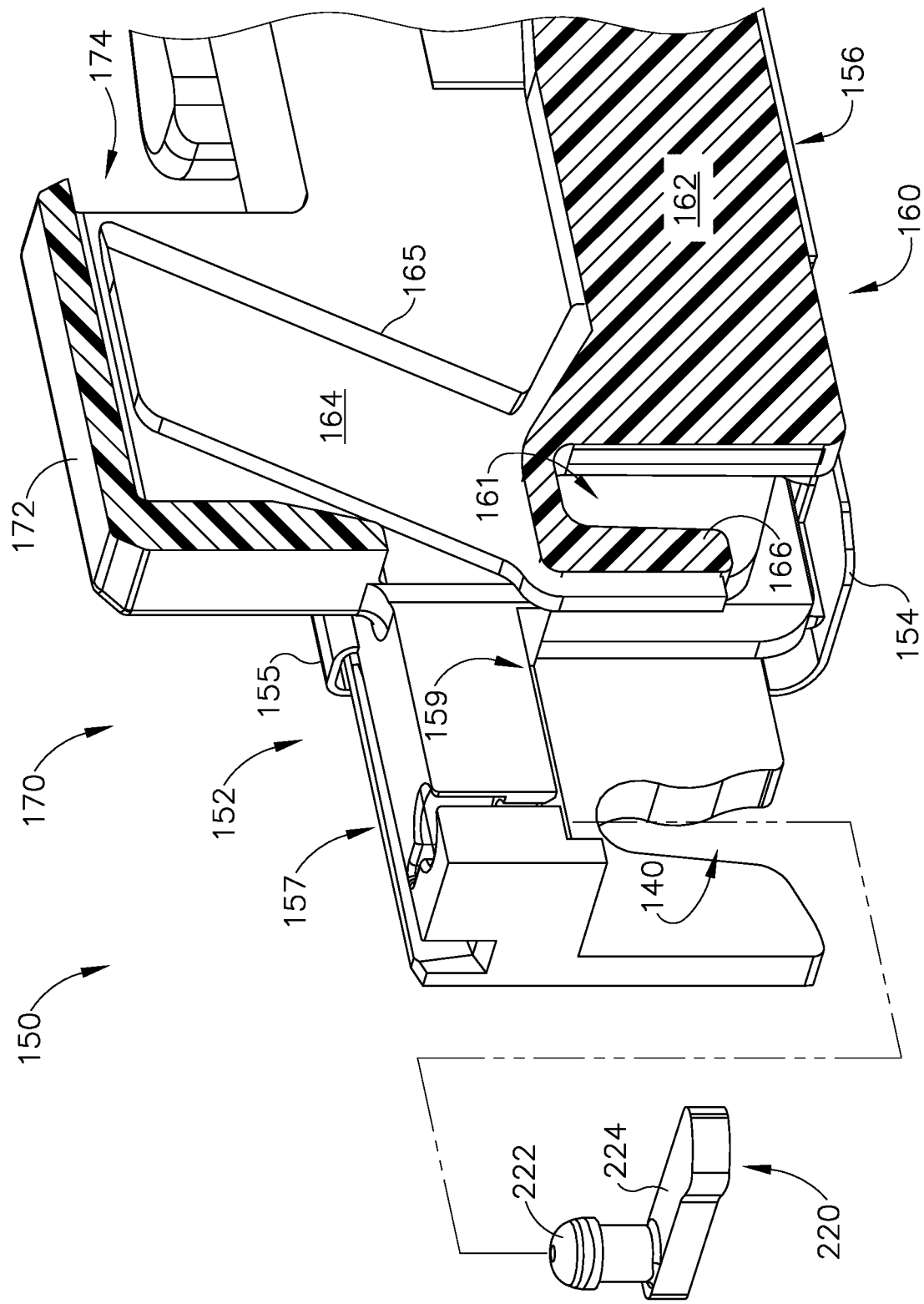
FIG. 13 depicts a cross-sectional exploded view of the staple cartridge assembly of FIG. 4, taken along line 12-12 of FIG. 5.

As best shown in FIGS. 12-13, staple cartridge assembly (150) defines both a pivot bore (157) and a sweep away recess (159). Additionally, lockout swing gate (220) includes a pivot post (222) and a leg (224). Pivot post (222) is rotationally housed within pivot bore (157). Leg (224) is configured to rotate from a first position (as shown in FIGS. 12, and 14A-15A) toward a second, disengaged, position (as shown in FIGS. 15B-15D) in response to suitable actuation of firing assembly (200). Leg (224) extends across slot (156) in the first position. Additionally, leg (224) is configured to urge actuating beam (202) into the unlocked configuration while in the first position. In the second position, leg (224) is housed within sweep away recess (159) such that leg (224) does not extend across slot (156), thereby preventing leg (424) from engaging actuating beam (202) while in the second position FIGS. 14A-14B show an exemplary loading of staple cartridge assembly (150) into staple cartridge channel (122). FIG. 14A shows staple cartridge assembly (150) aligned with staple cartridge channel (122) in preparation of loading. At this point, actuating beam (202) is in the pre-fired proximal position such that actuator (204) is in the position shown in FIG. 1. Leaf spring (113) biases actuating beam (202) into the locked configuration. In other words, leaf spring (113) biases actuating beam (202) away from staple cartridge channel (122) such that lockout block (125) rests within a cutout of actuating beam (202) partially defined by distally presented lockout face (214). At this point, if an operator attempts to actuate firing assembly (200) from the pre-fired proximal position to a fired position in accordance with the description above, distally presented lockout face (214) would abut against lockout block (125), thereby preventing distal translation of actuating beam (202).

Next, as shown in FIG. 14B, an operator may suitably load staple cartridge assembly (150) into staple cartridge channel (122). At this point, leg (224) of lockout swing gate (220) is in the first position such that leg (224) abuts against platform (212) of actuating beam (202) in order to overcome the biasing force of leaf spring (113) and drive actuating beam (202) from the locked configuration toward the unlocked configuration. Additionally, a distal protrusion (210) of actuating beam (202) slides within cutout (161) of staple sled assembly (160), thereby suitably coupling staple sled assembly (160) with actuating beam (202). It should be understood that in examples where staple sled assembly (160) is associated with actuating beam (202) rather than staple cartridge assembly (150), actuating beam (202) and staple sled assembly (160) will already be suitable coupled. At this moment, an operator may suitably couple first portion (102) with second portion (104) and pivot end effector (120) from the open position to the fully closed position in accordance with the description above.

Figure 15A:
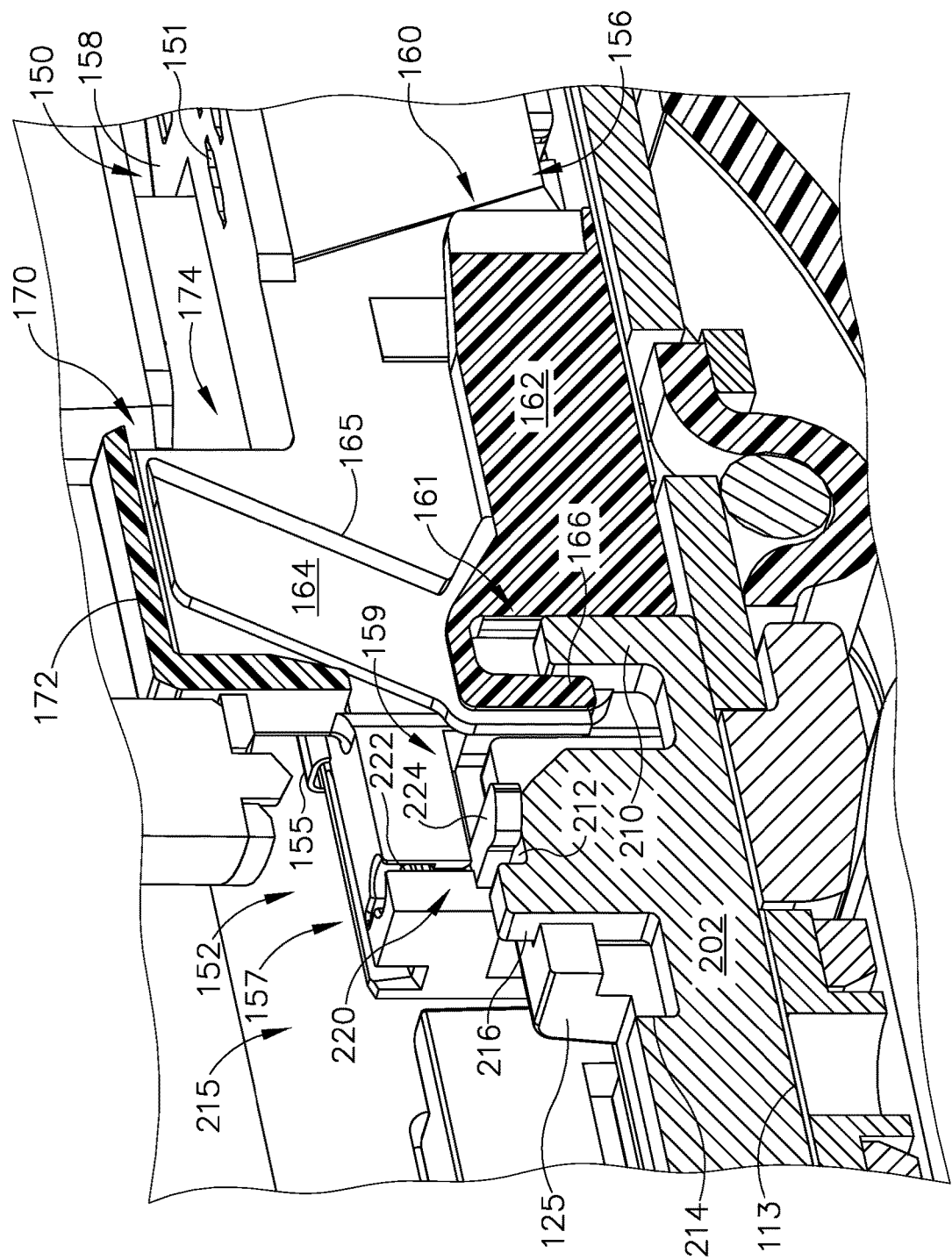
FIG. 15A depicts a cross-sectional perspective view of the first portion and the second portion of FIG. 10A in the fully closed position, where the firing assembly of FIG. 11A is in an unlocked configuration and a pre-fired position, taken along line 12-12 of FIG. 5.
Figure 15B:
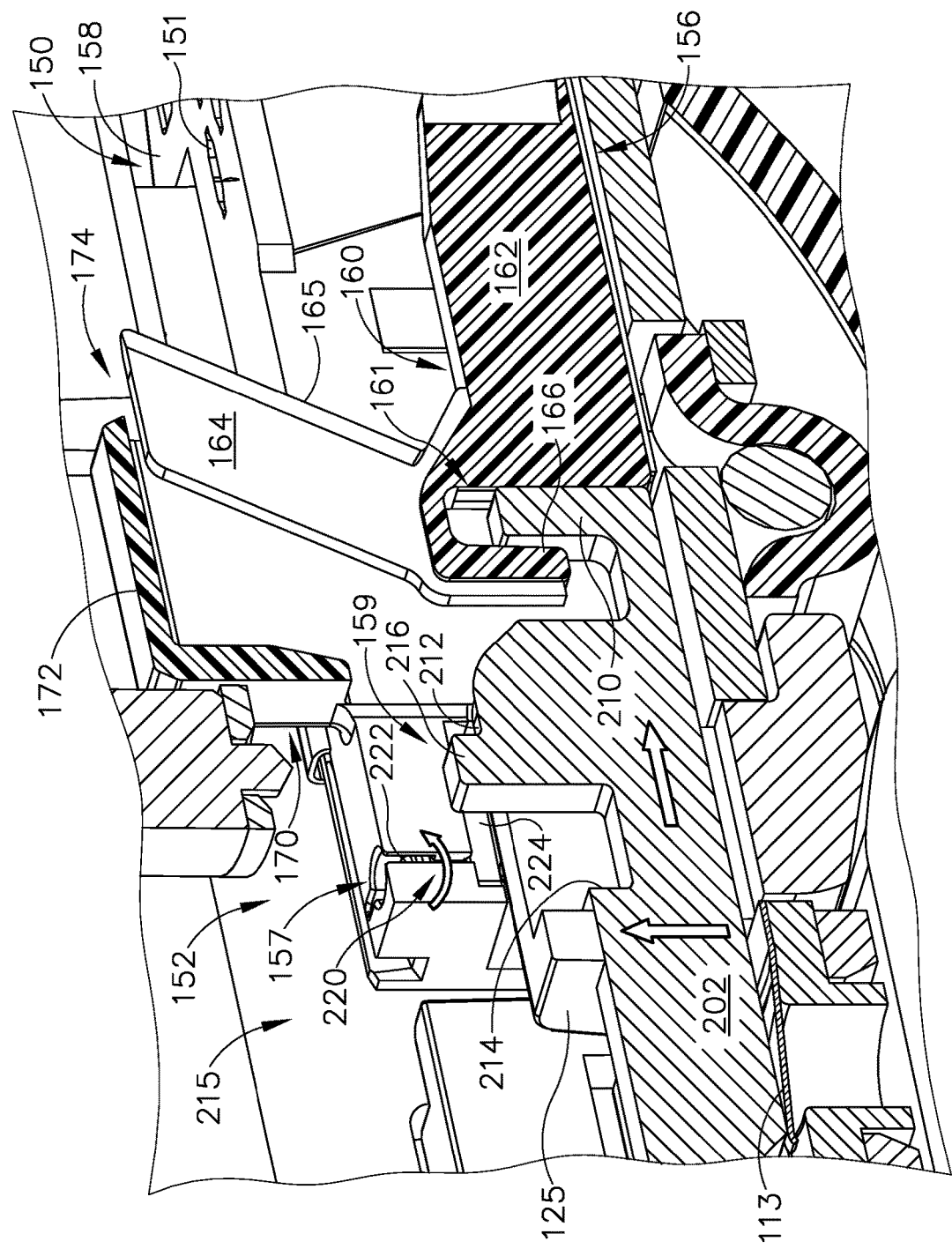
FIG. 15B depicts a cross-sectional perspective view of the first portion and the second portion of FIG. 10A in the fully closed position, where the firing assembly of FIG. 11A is in an unlocked configured and a partially fired position, taken along line 12-12 of FIG. 5.
Figure 15C:
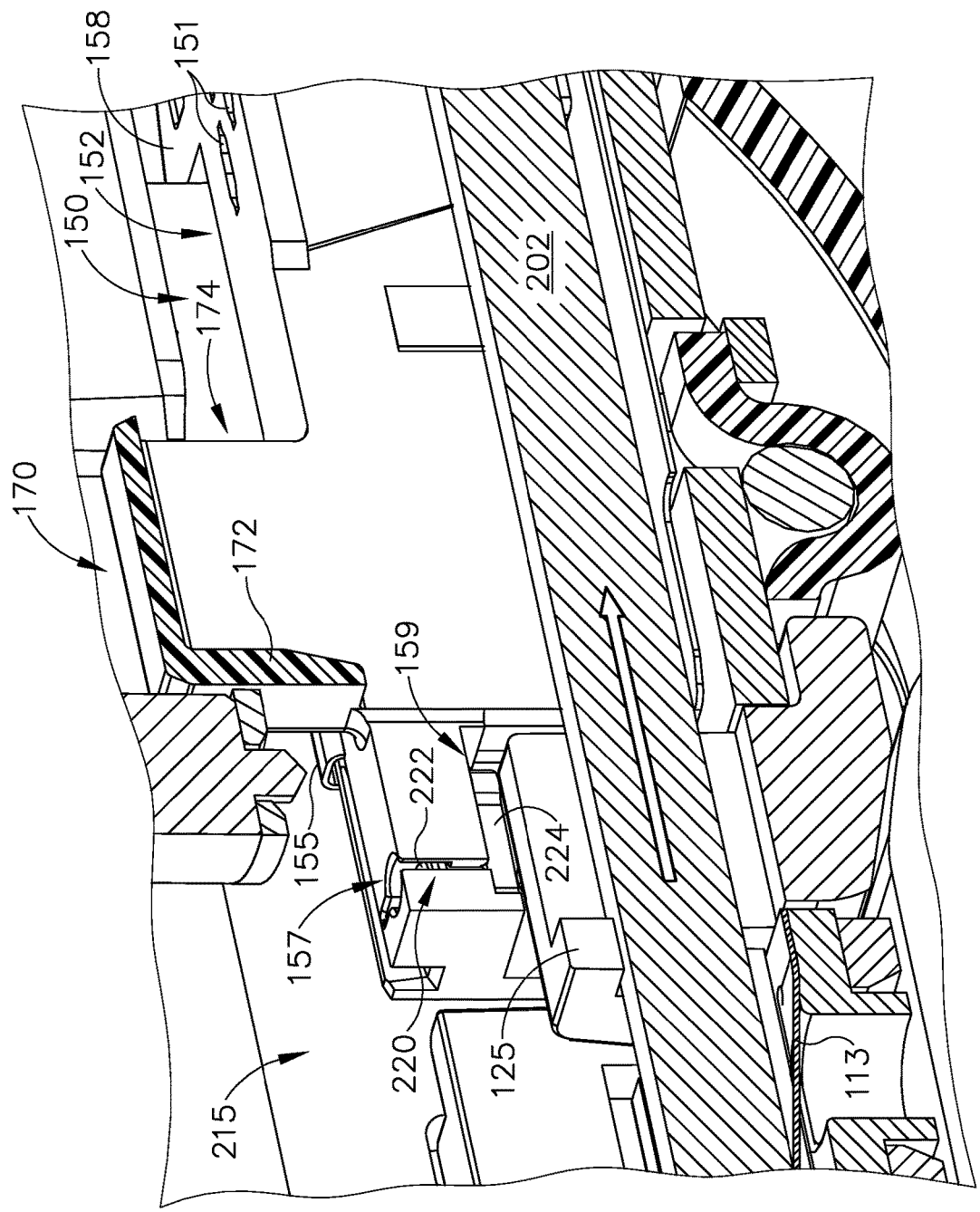
FIG. 15C depicts a cross-sectional perspective view of the first portion and the second portion of FIG. 10A in the fully closed position, where the firing assembly of FIG. 11A is in an unlocked configuration and a fired position, taken along line 12-12 of FIG. 5.
Figure 15D:
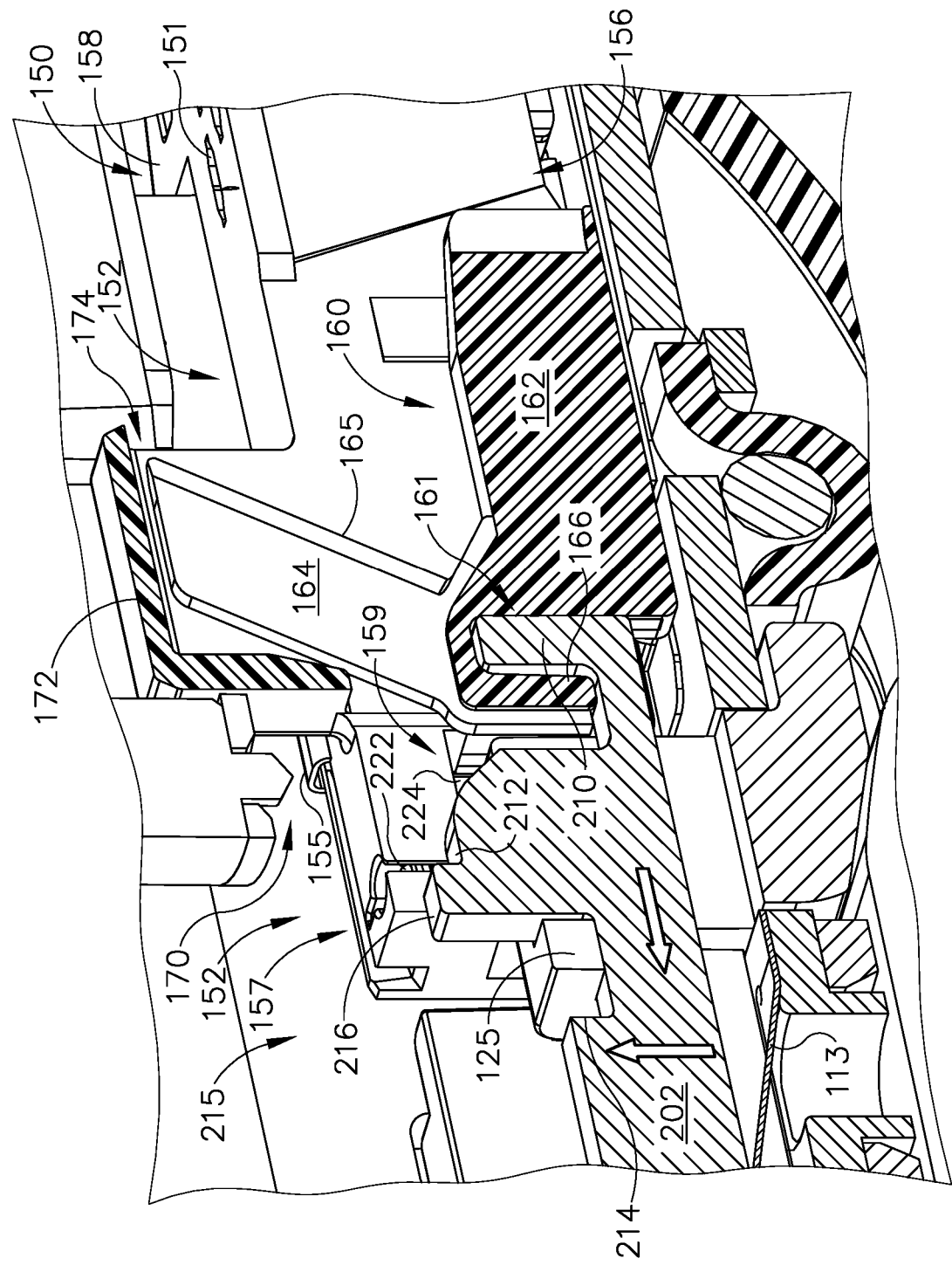
FIG. 15D depicts a cross-sectional perspective view of the first portion and the second portion of FIG. 10A in the fully closed position, where the firing assembly of FIG. 11A is in a locked configuration and a post-fired position, taken along line 12-12 of FIG. 5.

FIGS. 15A-15B show lockout assembly (215) during an exemplary firing of instrument (100) in accordance with the description above. FIG. 15A shows staple cartridge assembly (150) suitably loaded into staple cartridge channel (122) as described above, with end effector (120) in the fully closed position and firing assembly (200) in the pre-fired proximal position. Therefore, at this point, actuating beam (202) is urged into the unlocked configuration by leg (224) of lockout swing gate (220) such that lockout block (125) will not prevent distal translation of actuating beam (202). Next an operator may pivot and translate actuator (204) in order to actuate firing assembly in accordance with the description above.

As seen in FIG. 15B, distal actuation of firing assembly (200) causes a sweep away projection (216) of actuating beam (202) to rotate leg (224) of lockout swing gate (220) from the first position to the second position within sweep away recess (159) of cartridge body (152). Because leg (224) of lockout swing gate (220) no longer extends across slot (156) to abut against platform (212), leaf spring (113) may bias actuating beam (202) upward. However, it should be understood that distally presented lockout face (214) of actuating beam (202) has already translated distally past lockout block (125) such that lockout block (125) may not prevent distal translation of actuating beam (202) at this moment. Next, as seen in FIG. 15C, an operator may further translate actuating beam (202) and staple sled assembly (160) within staple cartridge assembly (152) in accordance with the description above to staple and sever tissue captured between end effector (120).

As shown in FIG. 15D, when an operator proximally translates actuating beam (202) and staple sled assembly (160) toward a post-fired proximal position, leg (224) of lockout swing gate (220) is still in the second position housed within sweep away recess (159) of cartridge body (152). Because leg (224) does not span across slot (156) in the second position, leg (224) may no longer may contact actuating beam (202) when coupled with staple cartridge channel (122). Therefore, leaf spring (113) may urge actuating beam (202) into the locked configuration, even though staple cartridge assembly (150) is still loaded into staple cartridge channel (122), thereby preventing a second firing of instrument (100) with the same staple cartridge assembly (150). If an operator desires to use instrument (100) again, an operator may remove the used staple cartridge assembly (150), replace it with a new staple cartridge assembly (150), and repeat the process in accordance with the description above.

II. EXEMPLARY LINEAR CUTTING STAPLER WITH ALTERNATIVE LOCKOUT ASSEMBLY

In some instances, an operator may accidentally translate actuator (204) distally from the pre-fired proximal position, while an un-used staple cartridge assembly (150) is suitably loaded, but prior to end effector (120) being latched into the fully closed position. For instance, an operator may suitably load staple cartridge assembly (150) into staple cartridge channel (120), pivotably couple first portion (102) with second portion (104) via grooves (115) and lateral projections (111), pivot end effector (120) to the partially closed position, then inadvertently partially translate actuator (204) distally such that sweep away projection (216) rotates leg (224) of lockout swing gate (220) into sweep away recess (159) without firing staples. The operator may then proximally translate actuator (204) back to the pre-fired proximal position, pivot end effector (120) to the fully closed position, and then attempt to completely actuate firing assembly (200) in accordance with the description above. However, due to the inadvertent translation of actuator (204), leg (224) may have been inadvertently pivoted to the second position within sweep away recess (159). With leg (224) in the second position, actuating beam (202) will be in the locked configuration such that staple cartridge assembly (150) will not be usable. Therefore, it may be desirable to prevent partial pre-firing of firing assembly (200) by providing a lockout assembly that is configured to keep firing assembly (200) in the locked configuration until end effector (120) is ready for firing; such as when end effector (120) is pivoted into the fully closed configuration.

Figure 16:
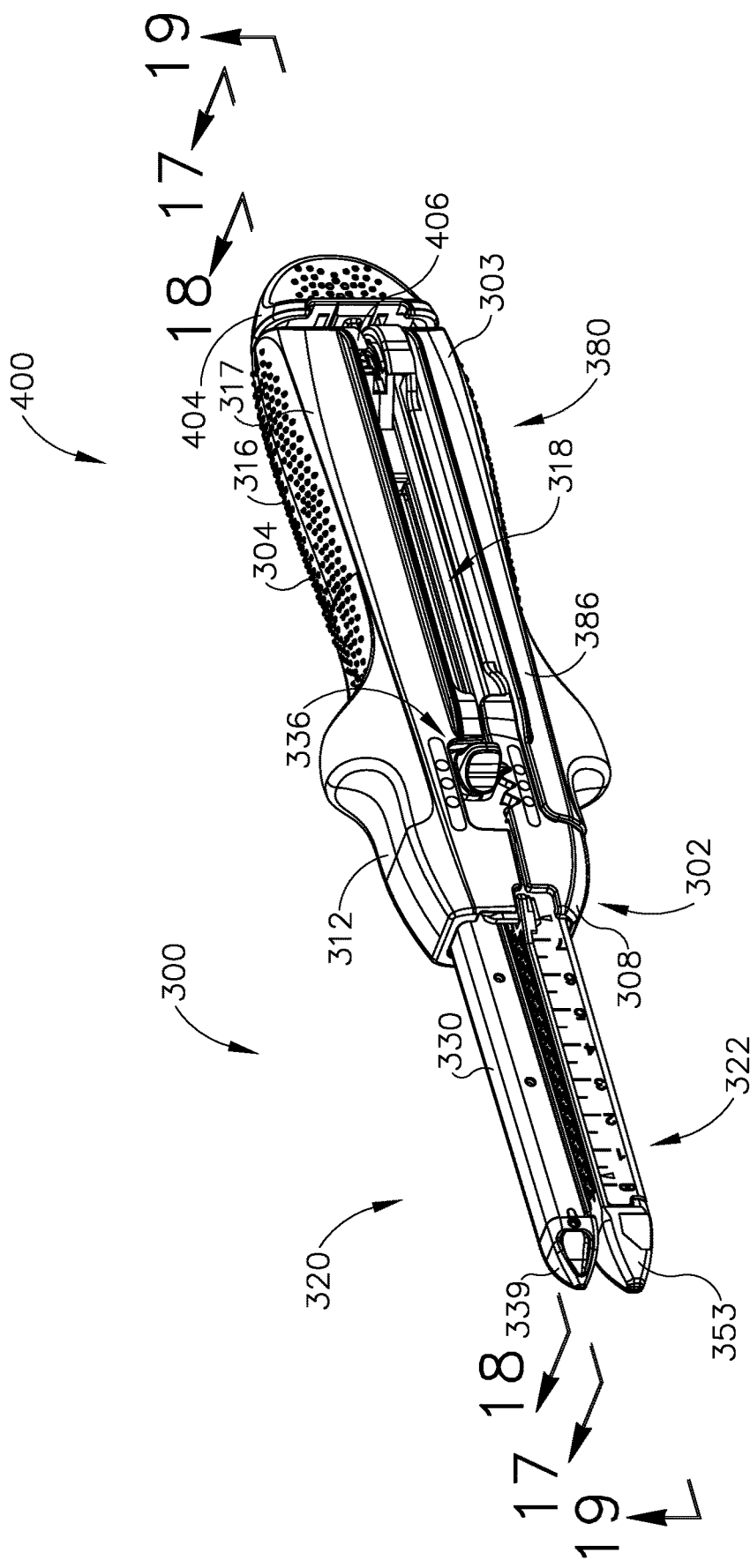
FIG. 16 depicts a perspective view of an exemplary alternative surgical stapling instrument that may be used in replacement of the surgical stapling instrument of FIG. 1.
Figure 17A:
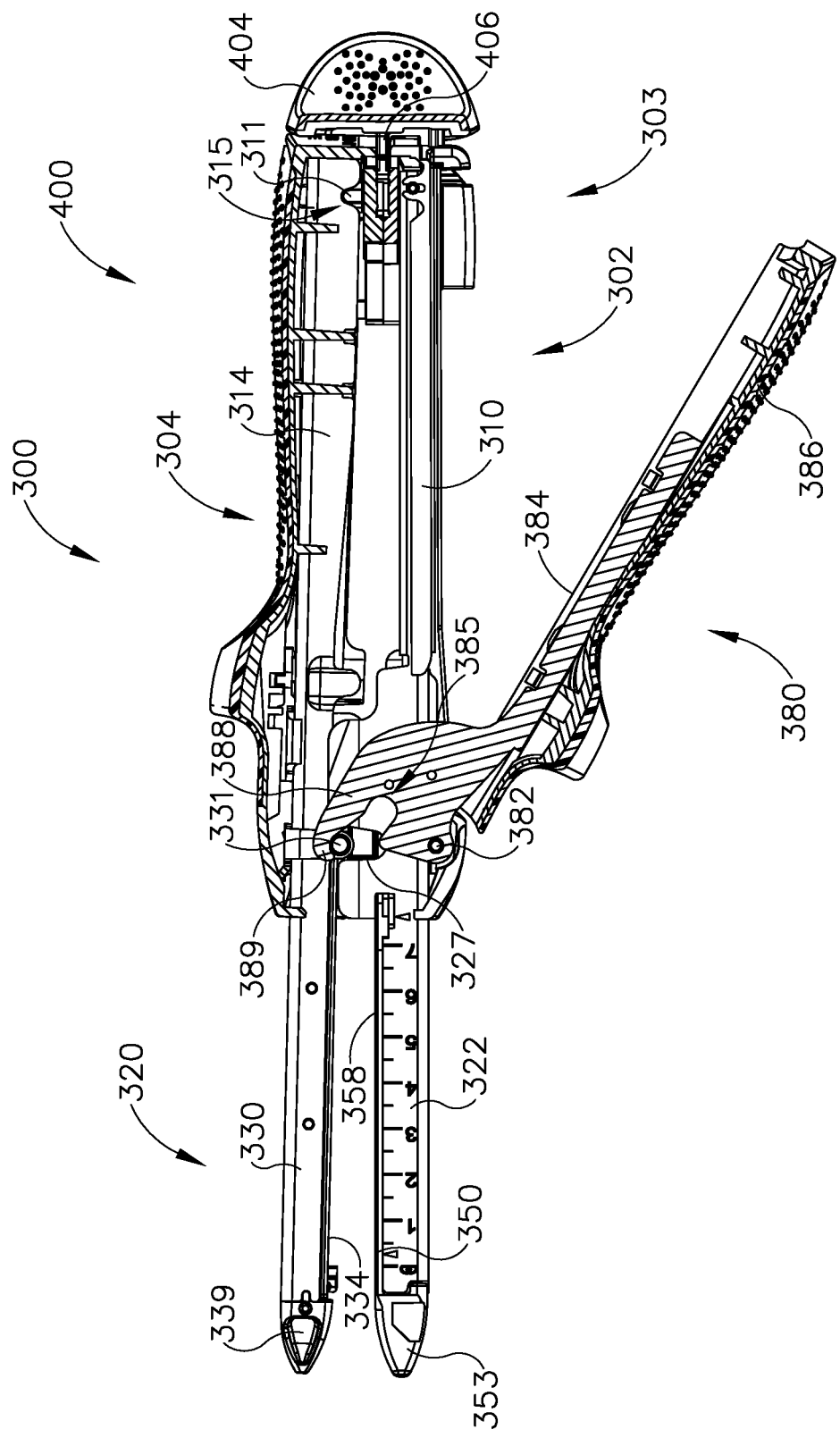
FIG. 17A depicts a cross-sectional side view of the surgical stapling instrument of FIG. 16 in a partially closed position, taken along line 17-17 of FIG. 16.
Figure 17B:
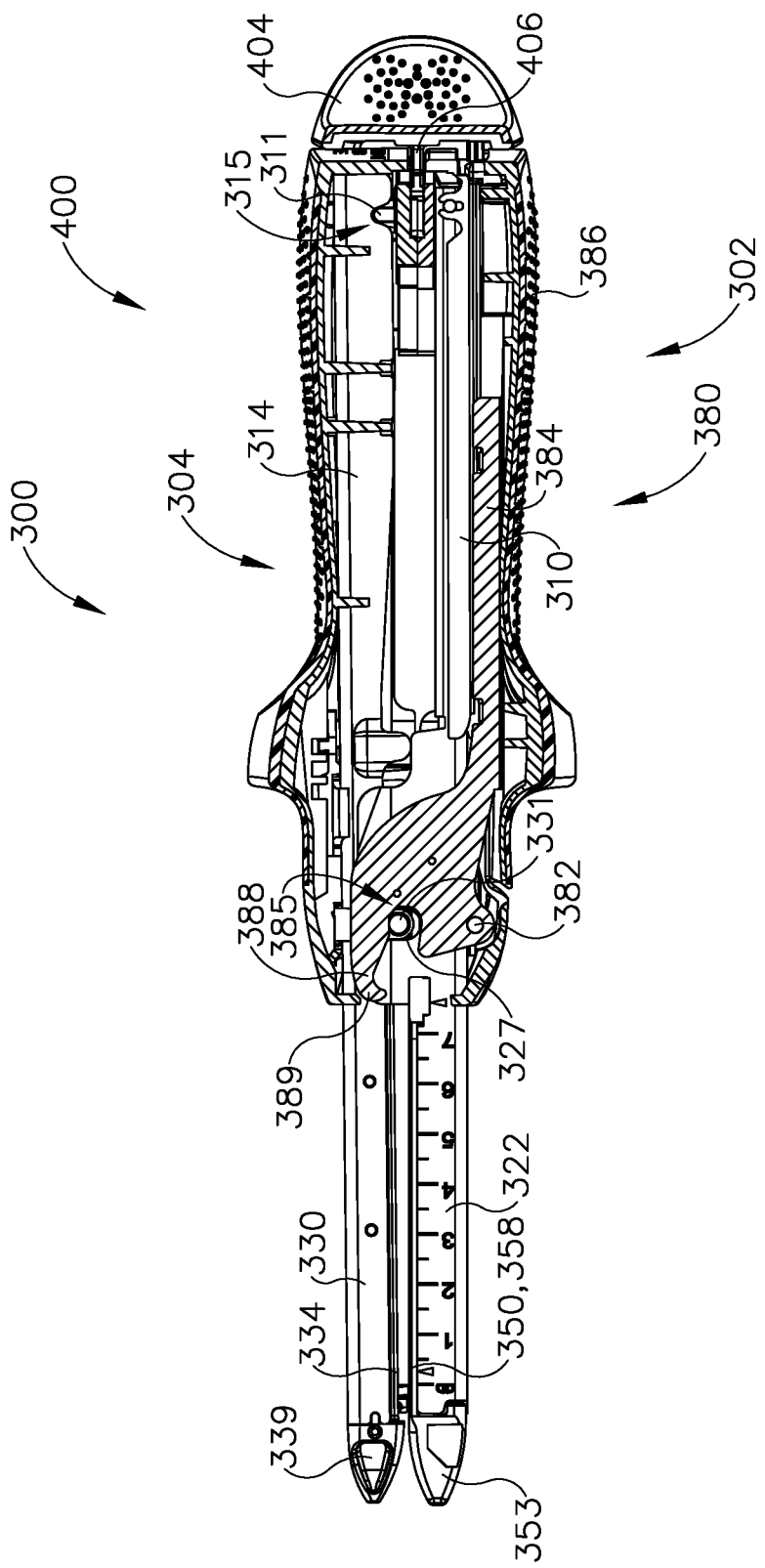
FIG. 17B depicts a cross-sectional side view of the surgical stapling instrument of FIG. 16 in a fully closed position, taken along line 17-17 of FIG. 16.

FIGS. 16-17B show an exemplary linear cutting stapler (300) configured to prevent firing of stapler (300) until an end effector (320) of stapler (300) is in the fully closed configuration with a suitably coupled, unfired, staple cartridge assembly (350). Linear cutting stapler (300) includes a first portion (302) having a staple cartridge channel (322), a second portion (304) having an anvil channel (330), staple cartridge assembly (350) that may selectively couple with cartridge channel (322) of first portion (302), and a firing assembly (400); which are substantially similar to first portion (102) having staple cartridge channel (122), second portion (104) having anvil channel (130), staple cartridge assembly (150) that may selectively couple with cartridge channel (122) of first portion (102), and firing assembly (200) described above, respectively, with differences elaborated below. Stapler (300) also includes a lockout assembly (415) configured to selectively prevent firing of stapler (300) as will be described in greater detail below.

Firing assembly (400) includes an actuating beam (402), a staple sled assembly (360), an actuator (404) (also referred to as a "firing knob"), and a pivot arm (406); which are substantially similar to actuating beam (202), staple sled assembly (160), actuator (204), and pivot arm (206) described above, respectfully, with differences elaborated below. Therefore, actuator (404) and pivot arm (406) may pivot from a proximal position to either lateral side of actuating beam (402), thereby enabling an operator to actuate firing assembly (400) from either a first side (316) or a second side (317) of instrument (300) when portions (302, 304) are properly coupled and end effector (320) is in the fully closed position. Additionally, first portion (302) and second portion (304) define a slot (318) dimensioned to accommodate translation of actuator (404).

Actuating beam (402) includes a distally presented lockout face (414) and a sweep away projection (416). As will be described in greater detail below, lockout face (414) is configured to prevent distal translation of actuating beam (402) while in the locked configuration; while sweep away projection (416) is configured to pivot a portion of lockout assembly (415) during distal translation of actuating beam (402).

First portion (302) includes a first proximal frame (310), staple cartridge channel (322), and a latching lever (380); which are substantially similar to first proximal frame (110), staple cartridge channel (122) and latching lever (180) described above, respectively. Therefore, first proximal frame (310) extends from a proximal end (103) distally into staple cartridge channel (322). First proximal frame (310) may be coupled with a handle cover (308), which may be substantially similar to handle cover (108) described above. Proximal end (303) includes one or more lateral pins, or projections (311), which may be substantially similar to projections (111) described above. Therefore, projections (311) are configured to receive grooves (315) of second portion (304) in order to initially pivotably couple first and second portions (302, 304). Staple cartridge channel (322) is dimensioned to selectively couple and decouple with staple cartridge assembly (350). Staple cartridge channel (322) defines notches or recesses (327). Recesses (327) are dimensioned to receive latch projections (331) of second portion (304) when second portion (304) pivots such that end effector (320) is in a fully closed position relative to first portion (302).

Latching lever (380) is pivotably coupled to either staple cartridge channel (322) or first proximal frame (310) via a pin (382). Latching lever (380) includes a proximal extending arm (384) and a distal latch body (388), which are substantially similar to proximal extending arm (184) and distal latch body (188) described above, respectively. Therefore, proximal extending arm (384) may be pivoted about pin (382) toward first proximal frame (310) in order to pivot distal latch body (388) toward staple cartridge channel (322) such that distal latch body (388) may engage and pivot second portion (304) toward first portion (302) to transition end effector (320) from a partially closed position (as shown in FIG. 17A) to a fully closed position (as shown in FIG. 17B). Proximally extending arm (384) may be coupled with an arm cover (386), that is substantially similar to arm cover (186) described above. Distal latch body (388) includes a pair of hooks (389), which are substantially similar to hooks (189) described above. Distal latch body (388) also defines a corresponding pair of latch cutouts (385), which are substantially similar to latch cutouts (185) described above.

As will be described in greater detail below, latching lever (380) includes a protrusion (387) configured to abut against a portion of a lockout assembly (415) such that lockout assembly (415) may selectively move actuating beam (402) from a locked configuration to an unlocked configuration when latching lever (380) pivots end effector (320) from the partially closed position to the fully closed position.

Staple cartridge assembly (350) includes a cartridge body (352), a pan (not shown), and a plurality of staple drivers (not shown), each configured to drive a respective staple (not shown); which are substantially similar to cartridge body (152), pan (154), and staple drivers (168) described above, respectively. Cartridge body terminates into a distal nose (353), which is substantially similar to distal nose (153) described above. Cartridge body (352) defines a plurality of staple cavities (not shown), a slot (356), and coupling cutouts (not shown), which are substantially similar to staple cavities (151), slot (156), and coupling cutouts (140) described above, respectively. Additionally, cartridge body (352) includes a staple deck (358), which is substantially similar to staple deck (158) described above. Sled assembly (360) includes a sled body (162) and a cutting member (364), which are substantially similar to sled body (162) and cutting member (164) described above, respectively.

Second portion (304) of instrument (300) includes a second proximal frame (314), anvil channel (330), latch projections (331), and an anvil plate (334), which is substantially similar to proximal frame (114), anvil channel (130), latch projections (131), and anvil plate (134) described above, respectively. Second proximal frame (314) may be coupled with a handle cover (312), which is substantially similar to handle cover (112) described above. Second portion (304) terminates distally in a distal nose (339), which is substantially similar to distal nose (139) described above. Second portion (404) of instrument (400) of the present example further includes a staple height adjustment mechanism (336), which may be substantially similar to staple height adjustment mechanism (136) described above.

FIGS. 18A-19C show exemplary lockout assembly (415) configured to lockout firing assembly (400) prior to end effector (320) being pivoted into the fully closed position with a suitably loaded unfired staple cartridge assembly (350). Additionally, similar to lockout assembly (215) described above, lockout assembly (415) is configured to lockout firing assembly (400) after actuating beam (402) and staple sled assembly (360) have been fired within staple cartridge assembly (350).

Lockout assembly (415) includes a lockout swing gate (420) pivotably coupled with a proximal end of cartridge body (352), a lockout block (325) fixed within staple cartridge channel (322), and a leaf spring (313) within staple cartridge channel (322). Leaf spring (313) is configured to bias actuating beam (402) into engagement with lockout block (325) when actuating beam (402) is in a proximal position, thereby urging actuating beam (402) into a locked configuration. In particular, distally presented lockout face (414) of actuating beam (402) may abut against lockout block (325) in the locked configuration, thereby preventing distal translation of actuating beam (402). While leaf spring (113) of stapler (100) was configured to bias actuating (202) away from staple cartridge channel (122); in the current example, leaf spring (313) is configured to bias actuating beam (402) toward staple cartridge channel (322).

As will be described in greater detail below, lockout swing gate (420) is configured to actuate relative to staple cartridge assembly (250) in order to engage and force actuating beam (402) out of alignment with lockout block (425), into an unlocked configuration, in response to end effector (320) pivoting into the fully closed position. Additionally, lockout swing gate (420) is also configured to pivot out of engagement with actuating beam (402) during distal actuation of firing assembly (400) such that lockout swing gate (420) is prevented from further engagement with actuating beam (402) after firing assembly (400) is actuated through a complete firing cycle in accordance with the description above. Therefore, after staple cartridge assembly (350) is used one time such that firing assembly (400) is actuated from a pre-fired proximal position into a post-fired proximal position, the previously used staple cartridge assembly (350) may be incapable of transitioning actuating beam (402) back into the unlocked configuration.

Staple cartridge assembly (350) defines both a pivot bore (357) and a sweep away recess (359). A circumferential flange (349) is located within the interior of pivot bore (357). As will be described in greater detail below, circumferential flange (349) may act as a floor support for lockout swing gate (420) such that lockout swing gate (420) may vertically actuate relative to pivot bore (357) without falling out of, or otherwise disassociating with, staple cartridge assembly (350). While in the current example, a circumferential flange (349) is used as a floor support for lockout swing gate (420), any other suitable floor support may be used as would be apparent to one having ordinary skill in the art in view of the teachings herein.

Figure 18A:
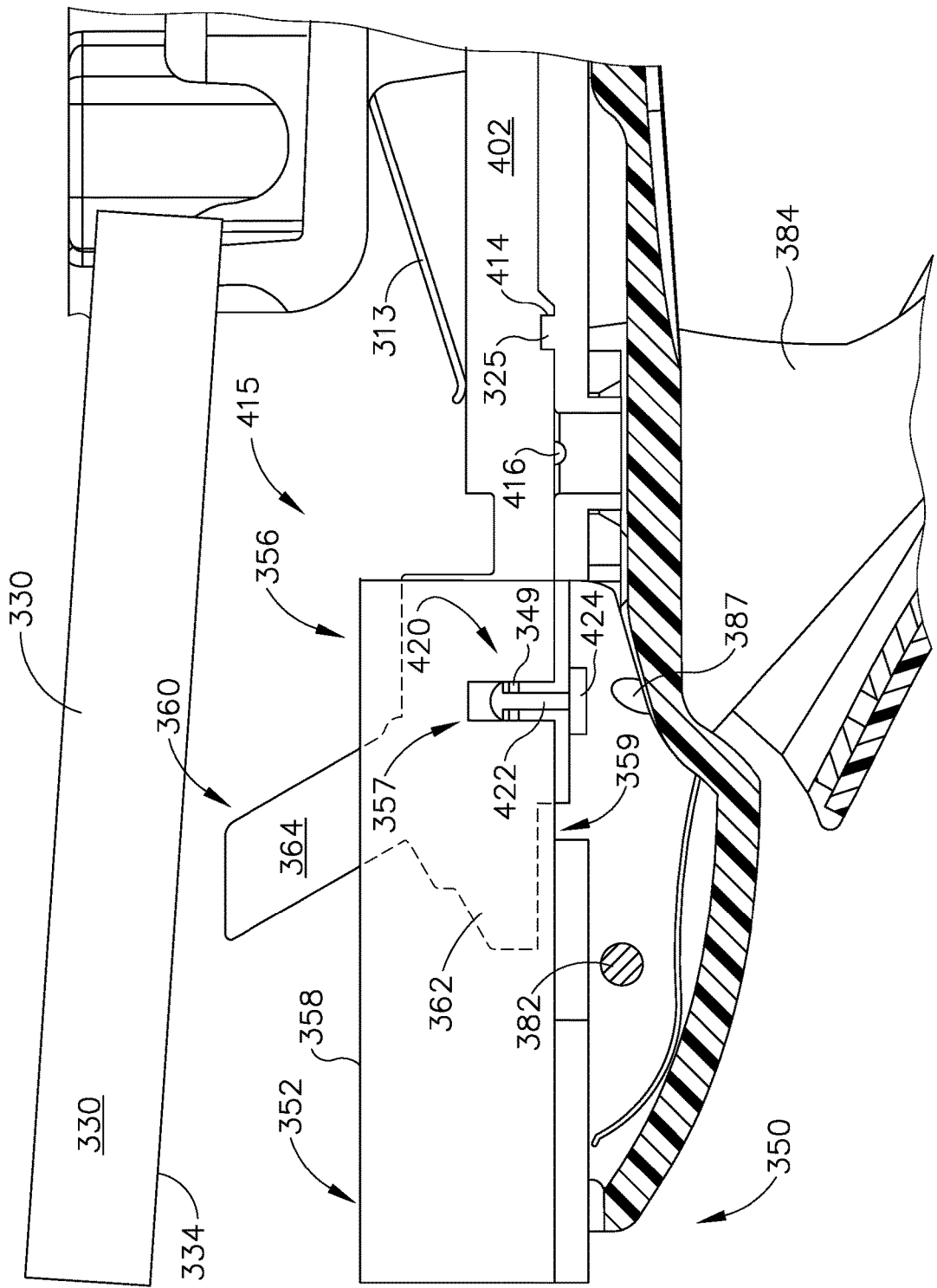
FIG. 18A depicts a cross-sectional side view of the surgical instrument of FIG. 16 in the partially closed position, where a firing assembly is in a locked configuration and a pre-fired position, taken along line 18-18 of FIG. 16.
Figure 18B:
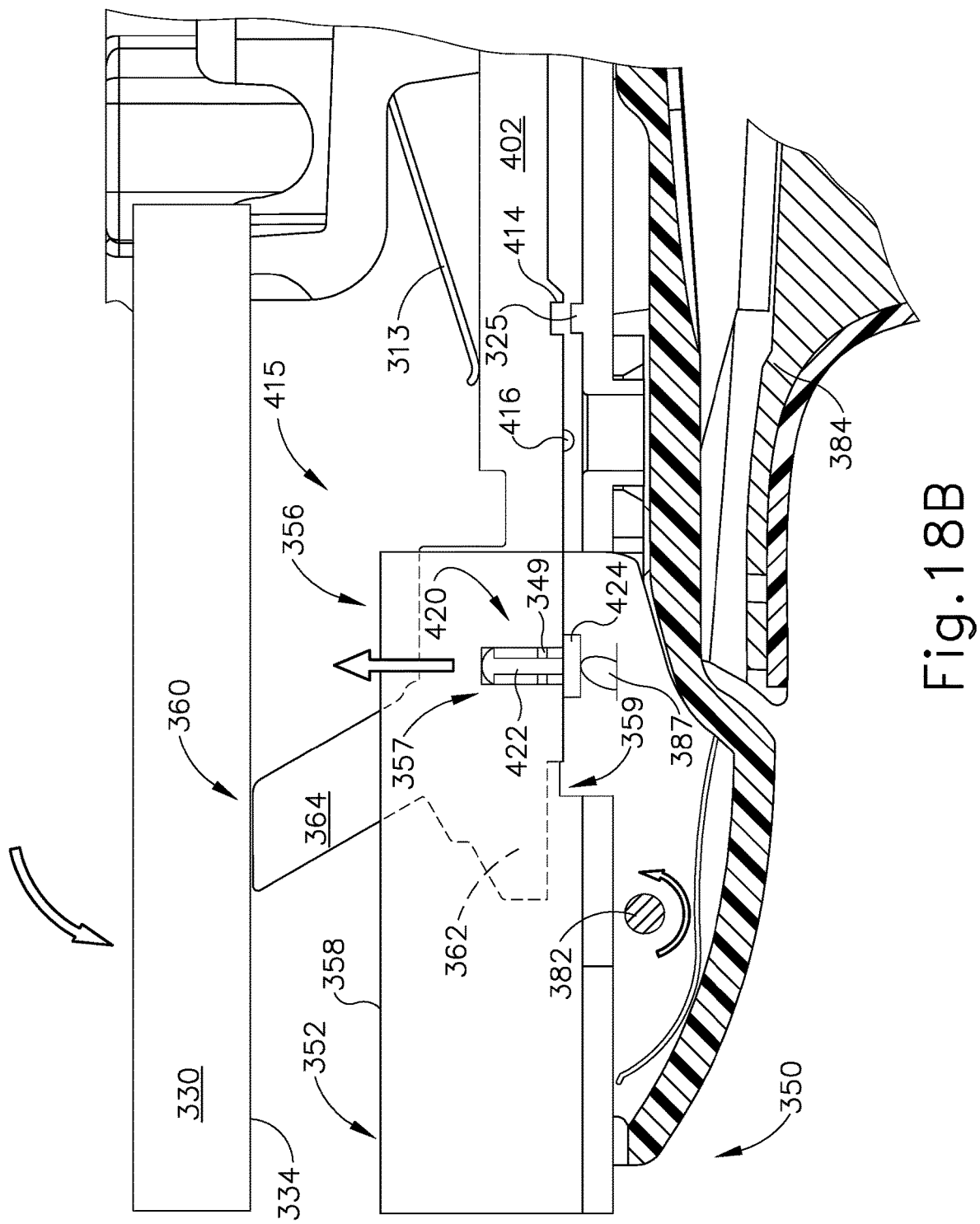
FIG. 18B depicts a cross-sectional side view of the surgical instrument of FIG. 16 in the fully closed position, where the firing assembly of FIG. 18A is in an unlocked configuration and a pre-fired position, taken along line 18-18 of FIG. 16.

Lockout swing gate (420) includes a pivot post (422) and a leg (424). Pivot post (422) is rotationally and slidably housed within pivot bore (357). In other words, pivot post (422) may rotate and translate within pivot bore (357). In particular, swing gate (420) is configured to actuate between a non-engageable position (as shown in FIG. 18A) and a engageable position (as shown in FIG. 18B) in response to the rotational position of latching lever (380). In particular, when latching lever (380) is not in the fully closed position, protrusion (387) does not make contact with swing gate (420) such that swing gate (420) is in the non-engageable position. However, protrusion (387) of latching lever (380) is dimensioned to abut against swing gate (420) when latching lever (380) pivots end effector (320) to the fully closed position. Protrusion (387) therefore drives swing gate (420) into the engageable position when end effector (320) is in the fully closed position.

Figure 18C:
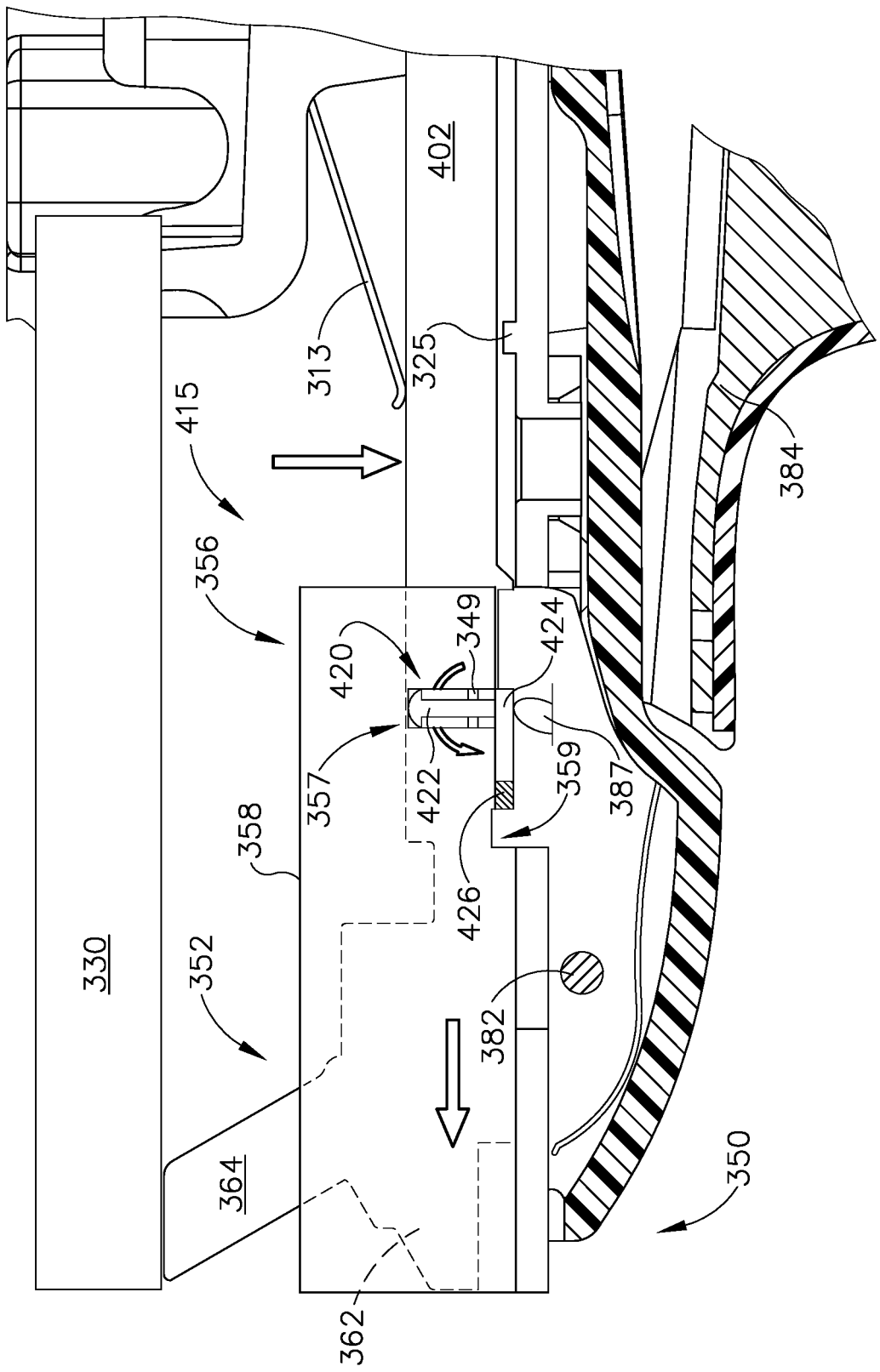
FIG. 18C depicts a cross-sectional side view of the surgical instrument of FIG. 16 in the fully closed position, where the firing assembly of FIG. 18A is in the unlocked configuration and a partially fired position, taken along line 18-18 of FIG. 16.
Figure 19A:
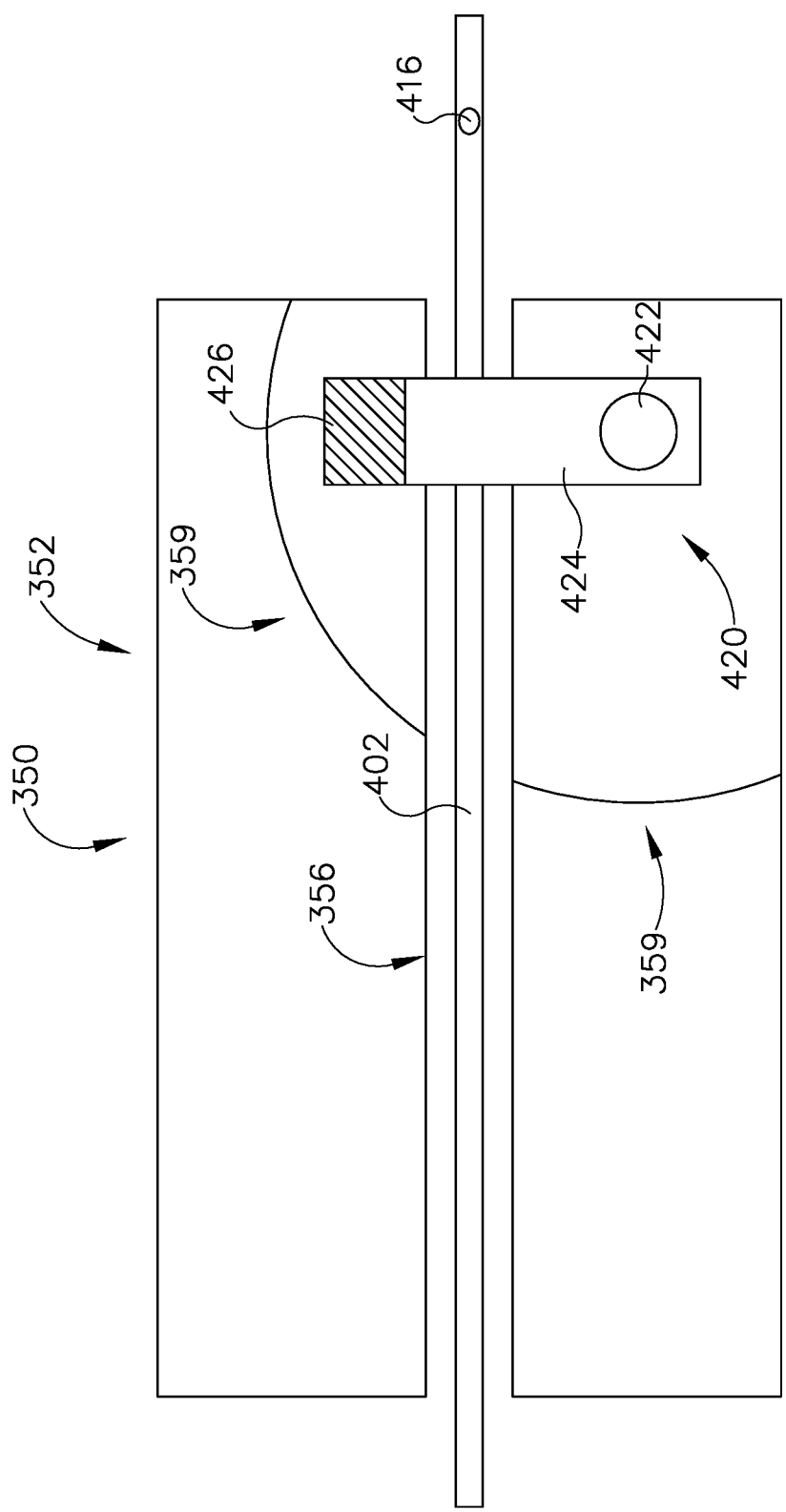
FIG. 19A depicts a cross-sectional bottom view of the surgical instrument of FIG. 16 in the fully closed position, where the firing assembly of FIG. 18A is in the unlocked configuration and the pre-fired position, taken along 19-19 of FIG. 16.
Figure 19B:
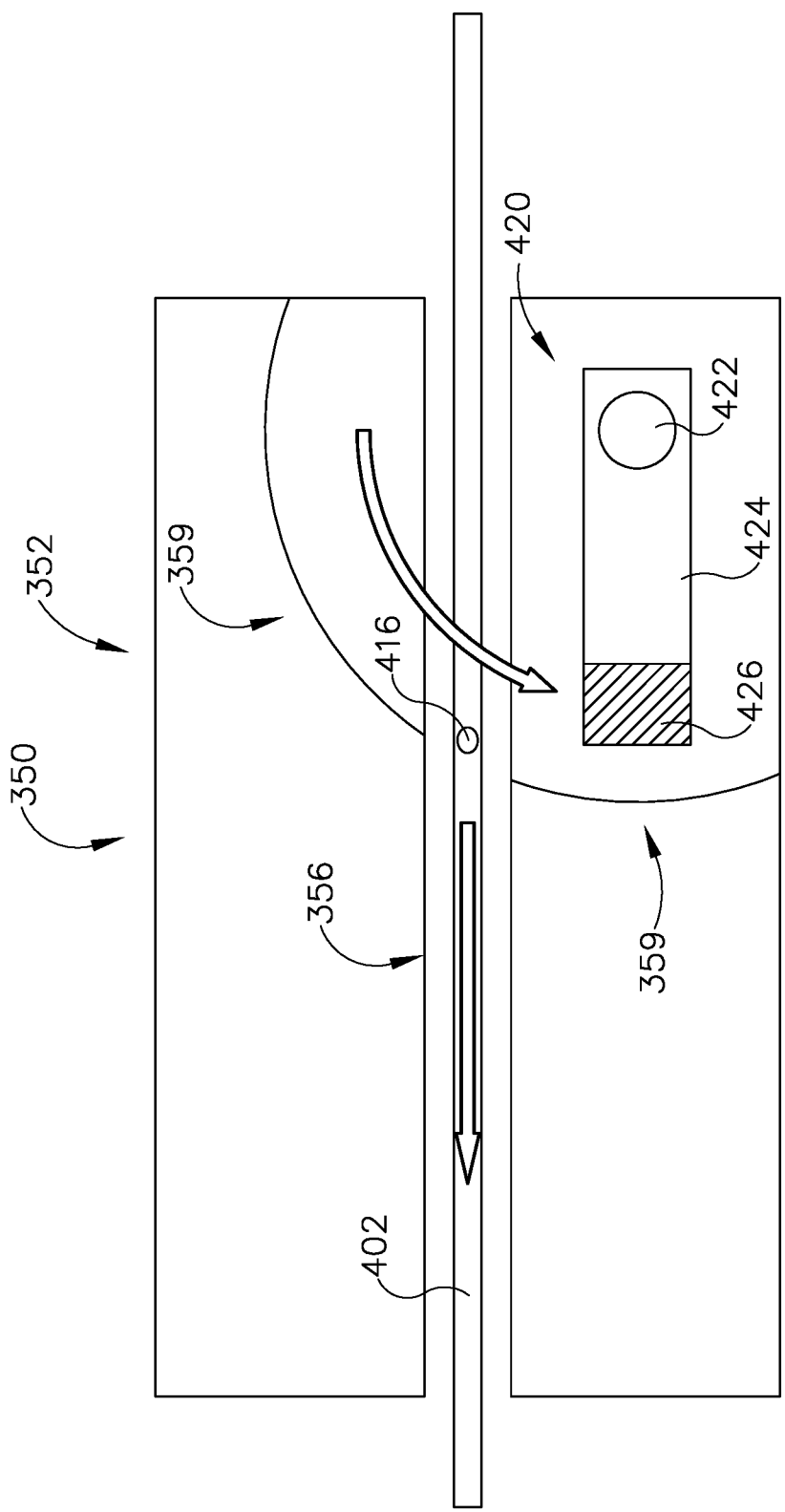
FIG. 19B depicts a cross-sectional bottom view of the surgical instrument of FIG. 16 in the fully closed position, where the firing assembly of FIG. 18A is in the unlocked configuration and the partially fired position, taken along 19-19 of FIG. 16.
Figure 19C:
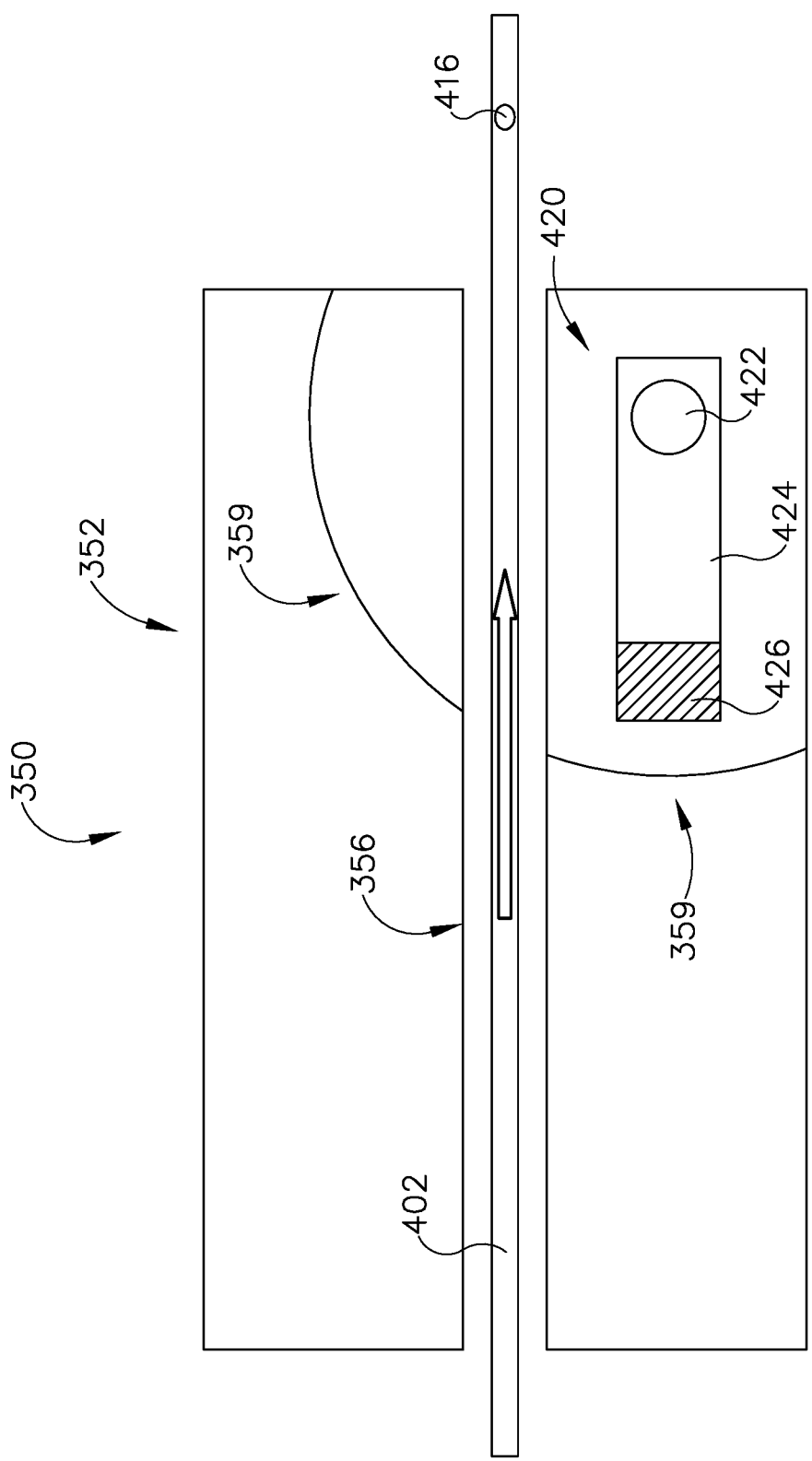
FIG. 19C depicts a cross-sectional bottom view of the surgical instrument of FIG. 16 in the fully closed position, where the firing assembly of FIG. 18A is in the locked configuration and the post-fired position, taken along 19-19 of FIG. 16.

Additionally, leg (424) is configured to rotate from a first rotational position (as shown in FIGS. 18A-18B and 19A) toward a second rotational position (as shown in FIGS. 18C and 19B-19C) in response to distal actuation of firing assembly (400). Leg (424) extends across slot (356) of cartridge body (352) in the first rotational position, while leg (424) does not extend across slot (356) of cartridge body (352) in the second rotational position. As will be described in greater detail below, actuating beam (402) of the firing assembly (400) includes a sweep away projection (416) configured to pivot leg (424) from the first rotational position to the second rotational position in response to distal translation of actuating beam (402).

Depending on the rotational position of leg (424), swing gate (420) may be configured to drive actuating beam (402) between the locked configuration and the unlocked configuration based on swing gate (420) actuating between the non-engageable position and the engageable position. In particular, as will be described in greater detail below, when leg (424) is in the first rotational position, actuation of swing gate (420) between the non-engageable position and the engageable position may drive actuating beam (402) between the locked position and the unlocked position, respectively. However, when leg (424) is in the second rotational position, actuation of swing gate (420) between the non-engageable position and the engageable position may not drive actuating beam (402) between the locked position and the unlocked portions.

Alternatively, when leg (424) is in the second rotational position, swing gate (420) may be prevented from even actuating to the engageable position. In other words, when leg (424) is in the first rotational position, latching lever (380) may pivot such that end effector (320) transitions between the partially closed position and the fully closed position in order to control whether actuating beam (402) is in the locked configuration or the unlocked configuration, respectively. However, when leg (424) is in the second rotational position, latching lever (380) is not capable of controlling whether actuating beam (402) is in the locked or unlocked configuration.

FIGS. 18A-19C show an operation of lockout assembly (415) during exemplary use of stapler (300) in accordance with the description above. FIG. 18A shows lockout assembly (415) while end effector (320) is in the partially closed position (as also shown in FIG. 17A) with a pre-fired staple cartridge assembly (350) suitably loaded into staple cartridge channel (322). Therefore, it should be understood that lateral projections (311) are housed within groves (315) to initially pivotally couple first portion (302) with second portion (304), and distal latch body (388) has being pivoted to initially engage latch projections (331) of second portion (304). While end effector (320) is in the partially closed position and firing assembly (400) is in the pre-fired proximal position, leaf spring (313) urges actuating beam (402) toward staple cartridge channel (322) such that distally presented lockout face (414) and lockout block (325) prevent distal actuation of firing assembly (400).

Leg (424) of lockout swing gate (420) is initially in the first position, where leg (424) extends across slot (356) of cartridge body (352) (as shown in FIG. 19A). As mentioned above, pivot post (422) of lockout swing gate (420) is slidably housed within pivot bore (357) while circumferential flange (349) acts as a floor support to prevent pivot post (422) from falling out of pivot bore (357). As also mentioned above, latching lever (380) includes a protrusion (387) dimensioned to abut against lockout swing gate (420) when latching lever (380) pivots end effector (320) in the fully closed position and leg (324) is in the first rotational position. However, since latching lever (380) is in the position associated with end effector (320) being in the partially closed position, protrusion (387) is not engaged with leg (424). Therefore, leaf spring (313) biases actuating beam (402) toward staple cartridge channel (322), while leg (324) of lockout swing gate (420) is in the non-engageable position. Because circumferential flange (348) acts as a floor support, pivot post (422) is prevented from falling out of pivot bore (357).

It should be understood that while lockout assembly (215) described above transitions actuating beam (202) into the unlocked configuration when a pre-fired staple cartridge assembly (150) is initially loaded; in the current lockout assembly (415), even though a pre-fired staple cartridge assembly (350) is suitably loaded into staple cartridge channel (322), and end effector (320) is pivoted to the partially closed position, actuating beam (402) is still locked out and prevented from being distally translated. This may help prevent against accidental distal translation of firing assembly (400).

Next, as shown in FIG. 18B, an operator may pivot latching lever (380) such that end effector (320) pivots to the fully closed position (as also shown in FIG. 17B) in accordance with the description above. At this point, latching lever (380) is pivoted about pivot pin (382) such that protrusion (387) abuts against leg (324) of lockout swing gate (420). Because pivot post (422) of lockout swing gate (420) is slidably housed within pivot bore (357), when protrusion (387) abuts against swing gate (420), swing gate (420) is actuated upwards within pivot bore (357) into the lifted position. Because leg (324) of lockout swing gate (420) is still in the first position extending across slot (356) (as shown in FIG. 19A), upward movement of swing gate (420) causes leg (324) to lift actuating beam (402) upwards, overcoming the biasing force of leaf spring (313), such that lockout face (414) is no longer in contact, or otherwise obstructed, by lockout block (325). With lockout face (414) no longer obstructed by lockout block (325), actuating beam (402) is in the unlocked configuration. In other words, when end effector (320) is pivoted to the fully closed position with a pre-fired staple cartridge assembly (350), actuating beam (402) transitions from the locked configuration toward the unlocked configuration.

With lockout assembly (415) urging actuating beam (402) into the unlocked configuration, an operator may then actuate firing assembly (400) distally in accordance with the description above. As best shown in FIGS. 18C and 19B, during initial distal actuation of firing assembly (400), sweep away projection (416) may contact leg (424) of lockout swing gate (420). Because pivot post (422) is pivotably coupled within pivot bore (357), contact between projection (416) and leg (424) pivots leg (424) from the first rotational position to the second rotational position. As shown in FIG. 19B, when leg (424) is in the second position, leg (424) no longer extends across slot (356) of cartridge body (352). Therefore, leg (424) is no longer capable of engaging actuating beam (402), such that leaf spring (313) may bias actuating beam (402) back toward staple cartridge channel (322).

Figure 18D:
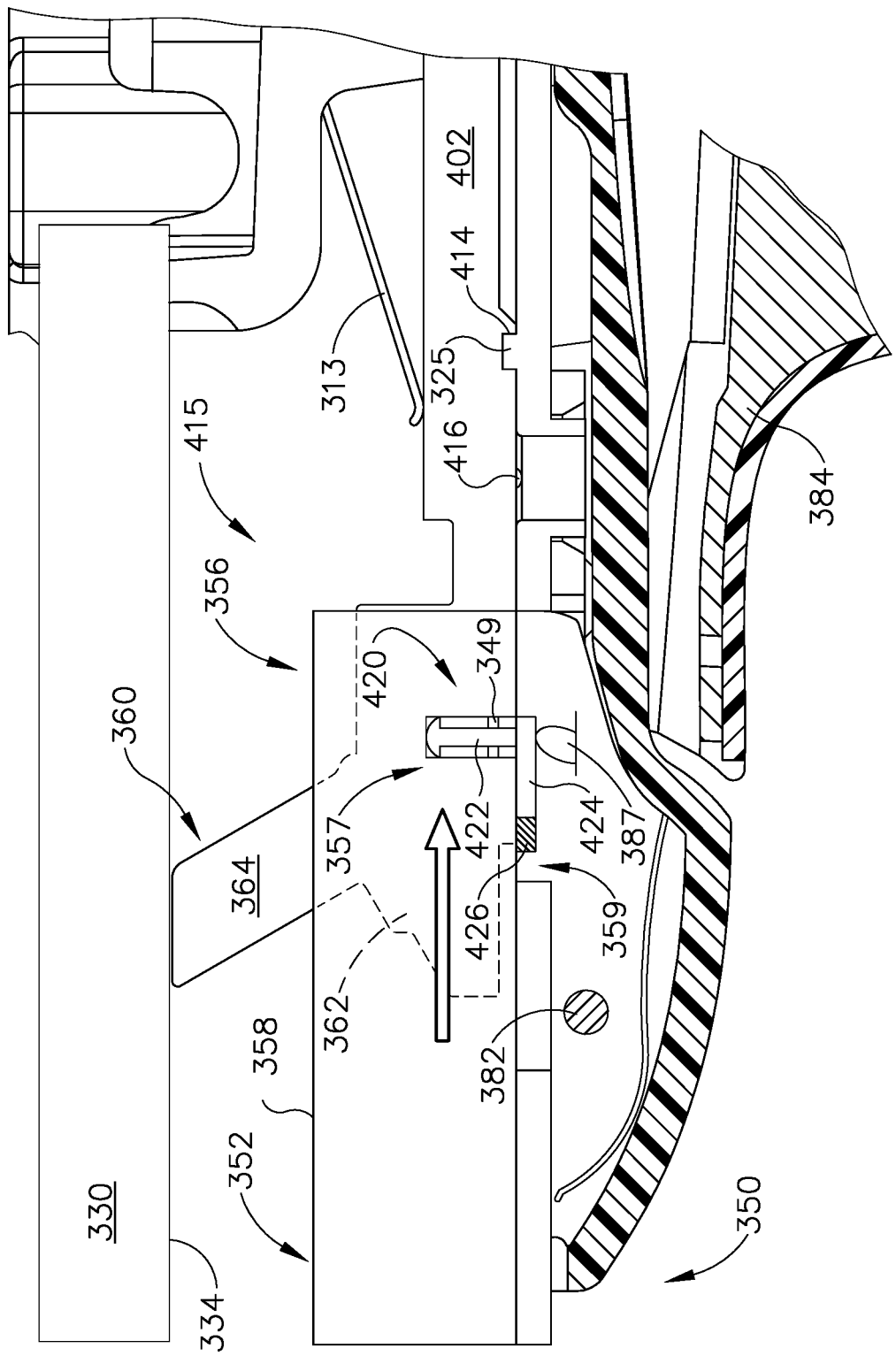
FIG. 18D depicts a cross-sectional side view of the surgical instrument of FIG. 16 in the fully closed position, where the firing assembly of FIG. 18A is in the locked configuration and a post-fired position, taken along line 18-18 of FIG. 16.

As best seen in FIGS. 18D and 19C, once firing assembly (400) has been fired and retracted in accordance with the description above such that actuating beam is in the post-fired proximal position, leaf spring (313) biases actuating beam (402) such that lockout face (414) is obstructed by lockout block (325). Because leg (424) of a used staple cartridge assembly (350) is in the second rotational position in response to distal translation of actuating beam (402), leg (424) is not capable of engaging actuating beam (402) in the post-fired proximal position, even when latching lever (380) pivots end effector (320) is in the closed position. Therefore, if an operator attempts to use stapler (300) a second time with the same staple cartridge assembly (350), lockout assembly (415) will prevent the operator from actuating firing assembly (400).

Figure 20A:
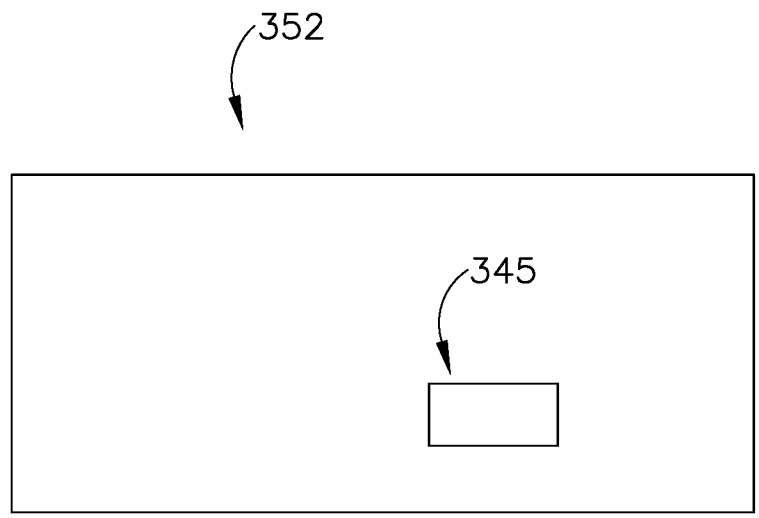
FIG. 20A depicts a side elevation view of a cartridge body of the surgical instrument of FIG. 16 in a pre-fired position.
Figure 20B:
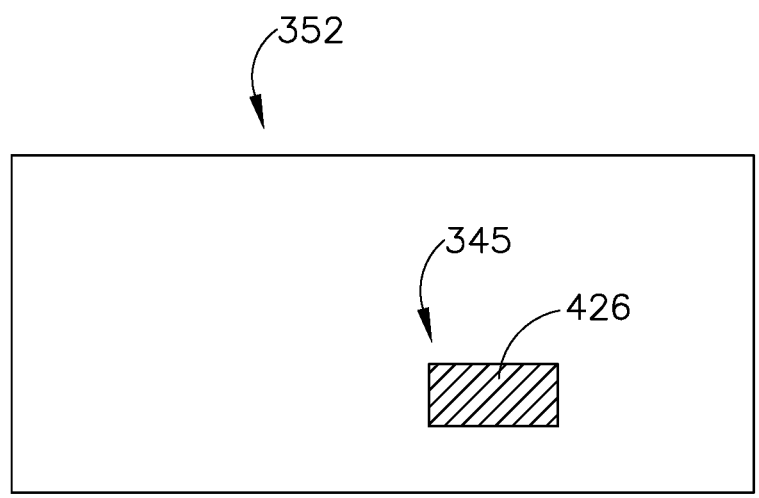
FIG. 20B depicts a side elevation view of the cartridge body of FIG. 20A in a post-fired position.

In some instances, it may be usefully to visually confirm if staple cartridge assembly (350) has been previously used or not. As shown in FIGS. 20A-20B, cartridge body (352) defines a viewing window (345). Additionally, leg (424) of lockout swing gate (420) includes an indicating portion (426). Indicating portion (426) may include a visual marking that is distinctive compared to the portion of cartridge body (352) defining viewing window (345). Viewing window (345) is located adjacent to sweep away recess (359) such that indicating portion (426) of leg (424) may be viewed from viewing window (345) when in leg (424) is in the second rotational position, but also such that indication portion (426) is not easily viewable when leg (424) is in the first rotational position. Because cartridge assembly (350) is effectively locked out when leg (424) is in the second rotational position while firing assembly (400) is in the proximal position, if an operator views indication portion (426) of leg (424) through viewing window (345), an operator may confirm that cartridge assembly (350) will not work in stapler (300) when coupled because firing assembly (400) will remain in the locked configuration. Therefore, when indicating portion (426) of leg (424) is viewable from viewing window (345) defined by cartridge body (352), an operator may be able to visually confirm that staple cartridge assembly (350) is not usable to staple and sever tissue in conjunction with the rest of stapler (300), and may be disposed of.

III. EXEMPLARY COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, the apparatus comprising: (a) a handle assembly, wherein the handle assembly comprises: (i) a first arm, (ii) a second arm, wherein the second arm is configured to pivotably couple with the first arm at a proximal pivot location, and (iii) a latching lever pivotably coupled with the first arm at a distal pivot location; (b) an end effector, wherein the end effector comprises: (i) a first jaw extending distally from the first arm, (ii) a second jaw extending distally from the second arm, wherein the second jaw is configured to pivot relative to the first jaw between an open configuration, a partially closed configuration, and a fully closed configuration, wherein the latching lever is configured engage the second arm or the second jaw to pivot the second jaw from the partially closed configuration toward the fully closed configuration, and (iii) a staple cartridge assembly comprising a cartridge body housing a plurality of staples, wherein the staple cartridge assembly is configured to couple with either the first jaw or the second jaw; (c) a firing assembly configured to actuate from a pre-fired proximal position toward a distal position in order to staple and sever tissue captured between the first jaw and the second jaw; and (d) a lockout assembly configured to prevent distal translation of the firing assembly in a locked configuration and allow distal translation of the firing assembly in an unlocked configuration, wherein the latching lever is configured to actuate the lockout assembly from the locked configuration to the unlocked configuration in response to the latching lever pivoting the second jaw from the partially closed configuration to the fully closed configuration while the firing assembly is in the pre-fired proximal position.

Example 2

The apparatus of Example 1, wherein the firing assembly is configured to actuate from the distal position to a post-fired proximal position.

Example 3

The apparatus of Example 2, wherein the lockout assembly configured to keep the firing assembly in the locked configuration when the firing assembly actuates from the distal position to the post-fired proximal position.

Example 4

The apparatus of Example 3, wherein the firing assembly comprises an actuating beam, wherein the lockout assembly comprises a biasing member configured to bias the actuating beam into the locked configuration.

Example 5

The apparatus of Example 4, wherein the lockout assembly further comprises a swing gate associated with the cartridge assembly, wherein the swing gate is configured to pivot between a first rotational position and a second rotational position in response to distal translation of the actuating beam.

Example 6

The apparatus of Example 5, wherein the swing gate is operable to actuate the firing assembly between the unlocked configuration and the locked configuration in the first rotational position.

Example 7

The apparatus of Example 6, wherein the swing gate is inoperable to actuate the firing assembly between the unlocked configuration and the locked configuration in the second rotational position.

Example 8

The apparatus of Example 7, wherein the swing gate comprises a pivot post and a leg.

Example 9

The apparatus of Example 8, wherein the cartridge assembly defines a pivot bore and a sweep away recess, wherein the pivot post is housed within the pivot bore, wherein the leg is housed within the sweep away recess.

Example 10

The apparatus of Example 9, wherein the pivot post is configured to translate and rotate within the pivot bore.

Example 11

The apparatus of any one or more of Examples 1 through 10, wherein the lockout assembly comprises a projection associated with the latching lever.

Example 12

The apparatus of Example 11, wherein the projection is configured actuate the lockout assembly from the locked configuration to the unlocked configuration.

Example 13

The apparatus of any one or more of Examples 1 through 12, wherein the firing assembly comprises a firing knob pivotably coupled with the first arm.

Example 14

The apparatus of any one or more of Examples 1 through 13, wherein the staple cartridge assembly further comprises a cutting member.

Example 15

The apparatus of Example 14, wherein the firing assembly comprises a firing beam having a distal projection, wherein the distal projection is operable to selectively couple with the cutting member of the staple cartridge assembly.

Example 16

An apparatus, the apparatus comprising: (a) a handle assembly, wherein the handle assembly comprises: (i) a first arm, (ii) a second arm, wherein the second arm is configured to pivotably couple with the first arm at a proximal pivot location, and (iii) a latching lever pivotably coupled with the first arm at a distal pivot location; (b) an end effector, wherein the end effector comprises: (i) a first jaw extending distally from the first arm, (ii) a second jaw extending distally from the second arm, wherein the latching lever is configured engage the second arm or the second jaw to pivot the second jaw from a partially closed configuration toward a fully closed configuration, and (iii) a staple cartridge assembly comprising a cartridge body housing a plurality of staples, wherein the staple cartridge assembly is configured to couple with either the first jaw or the second jaw; (c) a firing assembly configured to actuate from a pre-fired proximal position toward a distal position to staple tissue captured between the first jaw and the second jaw in the fully closed configuration, wherein the firing assembly is configured to actuate from the distal position to a post-fired proximal position; and (d) a lockout assembly configured actuate from a locked configuration to an unlocked configuration in response to the latching lever pivoting the second jaw from the partially closed configuration to the fully closed configuration, wherein the lockout assembly is configured to remain secured in the locked configuration when the firing assembly is in the post-fired proximal position.

Example 17

The apparatus of Example 16, wherein the lockout assembly comprises a lockout block associated with either the first jaw or the second jaw.

Example 18

The apparatus of Example 17, wherein the firing assembly comprises an actuating beam defining a cutout configured to abut against the lockout block in the locked configuration.

Example 19

The apparatus of Example 18, wherein the lockout assembly comprises a biasing member configured to bias the actuating beam toward the lockout block.

Example 20

An apparatus, the apparatus comprising: (a) a handle assembly, wherein the handle assembly comprises: (i) a first arm, (ii) a second arm, wherein the second arm is configured to pivotably couple with the first arm at a proximal pivot location, and (iii) a latching lever pivotably coupled with the first arm at a pivot location; (b) an end effector, wherein the end effector comprises: (i) a first jaw extending distally from the first arm, (ii) a second jaw extending distally from the second arm, wherein the second jaw is configured to pivot relative to the first jaw between an open configuration, a partially closed configuration, and a fully closed configuration, wherein the latching lever is configured engage the second arm or the second jaw to pivot the second jaw from the partially closed configuration toward the fully closed configuration, and (iii) a staple cartridge assembly comprising a cartridge body housing a plurality of staples, wherein the staple cartridge assembly is configured to couple with either the first jaw or the second jaw; (c) a firing assembly configured to actuate from a pre-fired proximal position toward a distal position in order to staple tissue captured between the first jaw and the second jaw; and (d) a lockout assembly configured to transition from a locked configuration to an unlocked configuration, wherein the lockout assembly is configured to prevent distal actuation of the firing assembly in a locked configuration, wherein the lockout assembly comprises: (i) a first projection associated with the latching lever, (ii) a second projection associated with the firing assembly, and (iii) a swing gate associated with the staple cartridge assembly, wherein the swing gate is configured to actuate between a non-engageable position and an engageable position in response to the first projection actuating the swing gate, wherein the swing gate is configured to rotate between a first rotational position and a second rotational position in response to the second projection rotating the swing gate, wherein the first projection is configured to only actuate into the unlocked configuration when the swing gate is in both the engageable position and the first rotational position

IV. MISCELLANEOUS

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed Feb. 6, 2018, published as U.S. Pub. No. 2019/0239881 on Aug. 8, 2019; U.S. application Ser. No. 15/889,374, entitled "Features to Align and Close Linear Surgical Stapler," filed Feb. 6, 2018, published as U.S. Pub. No. 2019/0239886 on Aug. 8, 2019; U.S. application Ser. No. 15/889,376, entitled "Releasable Coupling Features for Proximal Portions of Linear Surgical Stapler," filed Feb. 6, 2018, published as U.S. Pub. No. 2019/0239883 on Aug. 8, 2019; U.S. application Ser. No. 15/889,388, entitled "Firing Lever Assembly for Linear Surgical Stapler," filed Feb. 6, 2018, published as U.S. Pub. No. 2019/0239884 on Aug. 8, 2019; and U.S. application Ser. No. 15/889,390, entitled "Clamping Mechanism for Linear Surgical Stapler," filed Feb. 6, 2018, published as U.S. Pub. No. 2019/0239885 on Aug. 8, 2019. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
   (a) a handle assembly, wherein the handle assembly comprises:
      (i) a first arm,
      (ii) a second arm, wherein the second arm is configured to pivotably couple with the first arm at a proximal pivot location, and
      (iii) a latching lever pivotably coupled with the first arm at a distal pivot location;
   (b) an end effector, wherein the end effector comprises:
      (i) a first jaw extending distally from the first arm,
      (ii) a second jaw extending distally from the second arm, wherein the second jaw is configured to pivot relative to the first jaw between an open configuration, a partially closed configuration, and a fully closed configuration, wherein the latching lever is configured to engage the second arm or the second jaw to pivot the second jaw from the partially closed configuration toward the fully closed configuration, and
      (iii) a staple cartridge assembly comprising a cartridge body housing a plurality of staples, wherein the staple cartridge assembly is configured to couple with either the first jaw or the second jaw;
   (c) a firing assembly, configured to actuate from a pre-fired proximal position toward a distal position in order to staple and sever tissue captured between the first jaw and the second jaw, wherein the firing assembly is configured to actuate from the distal position to a post-fired proximal position; and
   (d) a lockout assembly configured to prevent distal translation of the firing assembly in a locked configuration and allow distal translation of the firing assembly in an unlocked configuration, wherein the latching lever is configured to actuate the lockout assembly from the locked configuration to the unlocked configuration in response to the latching lever pivoting the second jaw from the partially closed configuration to the fully closed configuration while the firing assembly is in the pre-fired proximal position, wherein the lockout assembly further comprises a swing gate associated with the cartridge assembly, wherein the swing gate is configured to pivot between a first rotational position and a second rotational position in response to the firing assembly actuating from the pre-fired proximal position toward the distal position, wherein the swing gate is operable to translate relative to the cartridge body to actuate the firing assembly between the unlocked configuration and the locked configuration in the first rotational position, wherein the lockout assembly is stuck in the locked configuration when both the swing gate is in the second rotational position and the firing assembly is in the post-fired proximal position.

2. The apparatus of claim 1, wherein the firing assembly comprises an actuating beam, wherein the lockout assembly comprises a biasing member configured to bias the actuating beam into the locked configuration.

3. The apparatus of claim 1, wherein the swing gate is inoperable to actuate the firing assembly between the unlocked configuration and the locked configuration in the second rotational position.

4. The apparatus of claim 3, wherein the swing gate comprises a pivot post and a leg.

5. The apparatus of claim 4, wherein the cartridge assembly defines a pivot bore and a sweep away recess, wherein the pivot post is housed within the pivot bore, wherein the leg is housed within the sweep away recess.

6. The apparatus of claim 5, wherein the pivot post is configured to translate and rotate within the pivot bore.

7. The apparatus of claim 1, wherein the lockout assembly comprises a projection associated with the latching lever.

8. The apparatus of claim 7, wherein the projection is configured actuate the lockout assembly from the locked configuration to the unlocked configuration.

9. The apparatus of claim 1, wherein the firing assembly comprises a firing knob pivotably coupled with the first arm.

10. The apparatus of claim 1, wherein the staple cartridge assembly further comprises a cutting member.

11. The apparatus of claim 10, wherein the firing assembly comprises a firing beam having a distal projection, wherein the distal projection is operable to selectively couple with the cutting member of the staple cartridge assembly.

12. An apparatus, the apparatus comprising:
(a) a handle assembly, wherein the handle assembly comprises:
  (i) a first arm,
  (ii) a second arm, wherein the second arm is configured to pivotably couple with the first arm at a proximal pivot location, and
  (iii) a latching lever pivotably coupled with the first arm at a distal pivot location;
(b) an end effector, wherein the end effector comprises:
  (i) a first jaw extending distally from the first arm,
  (ii) a second jaw extending distally from the second arm, wherein the latching lever is configured to engage the second arm or the second jaw to pivot the second jaw from a partially closed configuration toward a fully closed configuration, and
  (iii) a staple cartridge assembly comprising a cartridge body housing a plurality of staples, wherein the cartridge body defines a bore, wherein the staple cartridge assembly is configured to couple with either the first jaw or the second jaw;
(c) a firing assembly configured to actuate from a pre-fired proximal position toward a distal position to staple tissue captured between the first jaw and the second jaw in the fully closed configuration, wherein the firing assembly is configured to actuate from the distal position to a post-fired proximal position; and
(d) a lockout assembly comprising a swing gate configured to translate and rotate within the bore of the cartridge body, wherein the lockout assembly is configured to actuate from a locked configuration to an unlocked configuration in response to the latching lever pivoting the second jaw from the partially closed configuration to the fully closed configuration to thereby translate the swing gate within the bore of the cartridge body when the firing assembly is in the pre-fired proximal position, wherein the firing assembly is configured to pivot the swing gate within the bore of the cartridge body in response to actuating from the pre-fired proximal position toward the distal position, wherein the lockout assembly is configured to return to the locked configuration when the firing assembly is actuated into the post-fired proximal position, wherein the lockout assembly is configured to remain in the locked configuration in response to the latching lever pivoting the second jaw from the partially closed configuration to the fully closed configuration to thereby translate the swing gate within the bore of the cartridge body when the firing assembly is in the post-fired proximal position.

13. The apparatus of claim 12, wherein the lockout assembly comprises a lockout block associated with either the first jaw or the second jaw.

14. The apparatus of claim 13, wherein the firing assembly comprises an actuating beam defining a cutout configured to abut against the lockout block in the locked configuration.

15. The apparatus of claim 14, wherein the lockout assembly comprises a biasing member configured to bias the actuating beam toward the lockout block.

16. An apparatus, the apparatus comprising:
(a) a handle assembly, wherein the handle assembly comprises:
  (i) a first arm,
  (ii) a second arm, wherein the second arm is configured to pivotably couple with the first arm at a proximal pivot location, and
  (iii) a latching lever pivotably coupled with the first arm at a pivot location;
(b) an end effector, wherein the end effector comprises:
  (i) a first jaw extending distally from the first arm,
  (ii) a second jaw extending distally from the second arm, wherein the second jaw is configured to pivot relative to the first jaw between an open configuration, a partially closed configuration, and a fully closed configuration, wherein the latching lever is configured to engage the second arm or the second jaw to pivot the second jaw from the partially closed configuration toward the fully closed configuration, and
  (iii) a staple cartridge assembly comprising a cartridge body housing a plurality of staples, wherein the staple cartridge assembly is configured to couple with either the first jaw or the second jaw;
(c) a firing assembly configured to actuate from a pre-fired proximal position toward a distal position in order to staple tissue captured between the first jaw and the second jaw; and
(d) a lockout assembly configured to transition from a locked configuration to an unlocked configuration, wherein the lockout assembly is configured to prevent distal actuation of the firing assembly in a locked configuration, wherein the lockout assembly comprises:
  (i) a first projection associated with the latching lever,
  (ii) a second projection associated with the firing assembly, and
  (iii) a swing gate associated with the staple cartridge assembly, wherein the swing gate is configured to actuate between a non-engageable position and an engageable position in response to the first projection actuating the swing gate, wherein the swing gate is configured to rotate between a first rotational position and a second rotational position in response to the second projection rotating the swing gate,
wherein the first projection is configured to only actuate into the unlocked configuration when the swing gate is in both the engageable position and the first rotational position.

* * * * *